(12) United States Patent
Bernatchez et al.

(10) Patent No.: US 8,409,583 B2
(45) Date of Patent: Apr. 2, 2013

(54) ENGINEERED VERSIONS OF CGTB (β-1,3 GALACTOSYLTRANSFERASE) ENZYMES, WITH ENHANCED ENZYMATIC PROPERTIES

(75) Inventors: Stephane Bernatchez, Chelsea (CA); Michel Gilbert, Gatineau (CA); Warren Wakarchuk, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 362 days.

(21) Appl. No.: 12/596,759

(22) PCT Filed: Apr. 18, 2008

(86) PCT No.: PCT/CA2008/000738
§ 371 (c)(1),
(2), (4) Date: Dec. 11, 2009

(87) PCT Pub. No.: WO2008/128345
PCT Pub. Date: Oct. 30, 2008

(65) Prior Publication Data
US 2011/0111454 A1 May 12, 2011

Related U.S. Application Data

(60) Provisional application No. 60/925,451, filed on Apr. 20, 2007.

(51) Int. Cl.
*A61K 39/00* (2006.01)
*C12N 9/10* (2006.01)

(52) U.S. Cl. .................. 424/192.1; 435/193; 435/69.7; 435/97

(58) Field of Classification Search ................ 435/69.7, 435/97, 193; 424/192.1
See application file for complete search history.

(56) References Cited

U.S. PATENT DOCUMENTS 7,217,549 B2 * 5/2007 Gilbert et al. ................ 435/193
2004/0259140 A1 12/2004 Gilbert et al.

OTHER PUBLICATIONS

Sequence alignment between Seq ID No. 10 and AC: AAY97206.*
Wakarchuk, W. W. et al., Role of paired basic residues in the expression of active recombinant galactosyltransferases from the bacterial pathogen *Neisseria meningitidis*. Protein Engineering, 1998, vol. 11 No. 4 pp. 295-302.
Chiu, C. P.C. et al. Structural analysis of the sialyltransferase CstII from *Campylobacter jejuni* in complex with a substrate analog. Nat Struct Mol Biol., 2004, vol. 11. No. 2 pp. 163-170.
Dyson, M.R. et al. Production of soluble mammalian proteins in *Escherichia coli*: identification of protein features that correlate with successful expression. BMC Biotechnol., 2004, vol. 4 No. 4 pp. 1-17.
Kapust, R. B. et al. *Escherichia coli* maltose-binding protein is uncommonly effective at promoting the solubility of peptides to which it is fused. Protein Sci., 1999, vol. 8 No. 8 pp. 1668-1674.
Bernatchez, S. et al. Variants of the beta 1,3-galactosyltransferase CgtB from bacterium *Campylobacter jejuni* have distinct acceptor specificities. Glycobiology, Dec. 2007, vol. 17 No. 12 pp. 1333-1343.

* cited by examiner

*Primary Examiner* — Tekchand Saidha
(74) *Attorney, Agent, or Firm* — Nada Jain, P.C.

(57) ABSTRACT

CgtB proteins with enhanced beta 1,3-galactosaminyltransferase activity, nucleic acids that encode the CgtB proteins and methods for use of the CgtB proteins.

12 Claims, 8 Drawing Sheets

FIG. 1
A
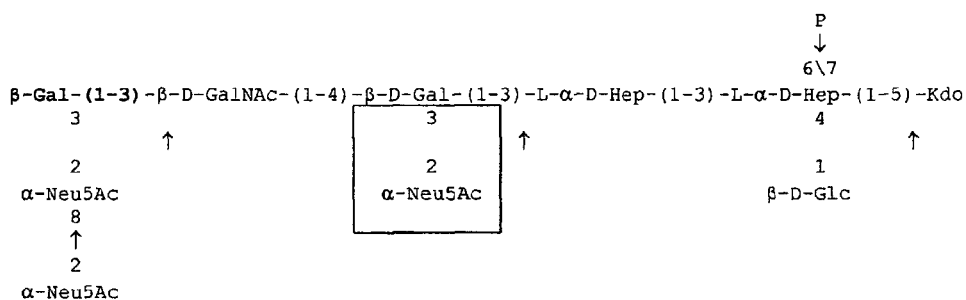
B
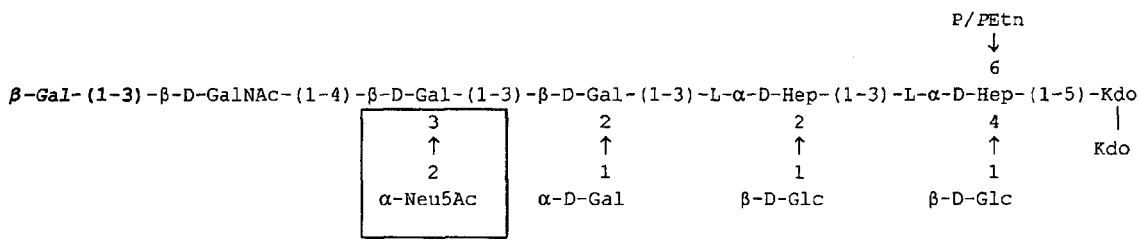
C
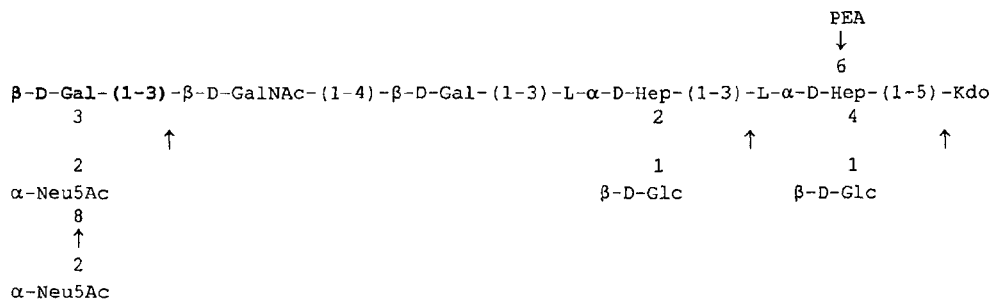

```
                 *         20         *         40         *         60
OH4384    : MEKISIILPTYNVEQYIARAIESCINQTFKDIEIIVVDDCGNDNSINIAKEYSKKDKRIK :  60
NCTC11168 : MSQISIILPTYNVEKYIAPALESCINQTFKDIEIIVVDDCGKDKSIDIAKEYASKDDRIK :  60
HS:10     : MEKISIILPTYNVEQYIARAIESCINQTFKNIEIIVVDDCGSDKSIDIVKEYAKKDDRIK :  60

*         80         *        100         *        120
OH4384    : IIHNEKNLGLLRARYEGVKVANSPYIMFLDPDDYLELNACEECIKILDEQD--EVDLVEI : 118
NCTC11168 : IIHNEENLKLLRARYECAKVATSPYIMFLDSDDYLELNACEECIKILDMGGGGKIDLLCI : 120
HS:10     : IIHNEENLKLLRARYEGVKVANSPYIMFLDPDDYLELNACEECMKILKNN---EIDLLEI : 117

*        140         *        160         *        180
OH4384    : NAIVESNVIS-YKKFDFNSGFYSKKEFVKKIIAKKNLYWTMMGKLIRKKLYIEAFASLRL : 177
NCTC11168 : EAFIT-NAKKSIKKLNIKDGKYNNKEFTMQILKTKNPFWTMKAKIIKKDIYLKAFNMLNL : 179
HS:10     : NAFVLENNNKIERKLNFQEKCYVKKDFLKELLKTKNLFWTVWAKVIKKELYLKAVGLISL : 177

*        200         *        220         *        240
OH4384    : EKDVKINMAEDVLLYYPYLSQAQKIAYMNCMLYHYVPNMMSICNTKNEVLVKNNIQELQL : 237
NCTC11168 : KKEIKINMAEDALLYYPITILSNEIFYLTQPLYTQHVNSNSITN--NINSLEANIQEHKE : 237
HS:10     : EN-AKINMAEDVLLYYPLINISNTESHLSKNLYNQINNFSITKELTLQNIKTNIQEQDN : 236

*        260         *        280         *        300
OH4384    : VLNYLRQN-MILNKYCSMYVLIKYLLYTQIYKFKRFKLEVTLLAKINILTLKILFKYKK : 296
NCTC11168 : VLNVLKSEKNKKTPLYFLIYYLLKIQLLKYEQNFN-KRNINLIYYKINILYQKYCFKWKK : 296
HS:10     : VLYLLKKMQMNYN-FNLTLLKLIEYFLLIEKYSFS-SK-RNVLCEKINIFFKKIQFKFYR : 293

OH4384    : FLKQC-- : 301
NCTC11168 : ELYNLIP : 303
HS:10     : LLKM--- : 297
```

B

|  | Whole enzyme | | NH₂-terminal domain | | COOH-terminal domain | |
|---|---|---|---|---|---|---|
|  | % identity | % similarity | % identity | % similarity | % identity | % similarity |
| CgtB$_{OH4384}$ vs. CgtB$_{11168}$ | 54 | 67 | 87 | 92 | 37 | 54 |
| CgtB$_{OH4384}$ vs. CgtB$_{HS:10}$ | 59 | 73 | 89 | 95 | 42 | 62 |
| CgtB$_{11168}$ vs. CgtB$_{HS:10}$ | 56 | 75 | 87 | 93 | 39 | 65 |

Fig. 5A

| Primer | Sequence | Relevant features |
|---|---|---|
| CJ-300 | 5'-CTTAGCGTCGACTTATTACATCTTCAGCAAGCGATAAAATTA-AATTG-3' | SalI site underlined, termination codon of cgtB<sub>OH4384</sub> in bold |
| CJ-301 | 5'-GCTGCTGGACATATGTTTAAATTTCAATCATCTTGCC-3' | NdeI site underlined, initiation codon of cgtB<sub>OH4384</sub> in bold |
| SCJ-319 | 5'-GCTGCTGGACATATGAGTCAAATTTCCATCATCATACTACCAAC-3' | NdeI site underlined, initiation codon of cgtB<sub>11168</sub> in bold |
| SCJ-322 | 5'-CTTAGCGTCGACTTAACATTGTTTAAAATTTTTTATATTT-3' | SalI site underlined, termination codon of cgtB<sub>OH4384</sub> in bold |
| SCJ-368 | 5'-CTTAGCGTCGACTTATTGAATTGATATTTTGATATATAAAATATT-3' | SalI site underlined, termination codon of cgtB<sub>11168</sub> in bold |
| SCJ-369 | 5'-CTTAGCGTCGACTTATATTTATAATAAGATTTATATTTCT-3' | SalI site underlined, termination codon of cgtB<sub>OH4384</sub> in bold |
| SCJ-370 | 5'-CTTAGCGTCGACTTATTTATTAAAATTTGTTCATATTTCAATAA-3' | SalI site underlined, termination codon of cgtB<sub>11168</sub> in bold |
| SCJ-400 | 5'-GCTGCTGGACATATGTTTAAAATTTCAATCATCTTACCAAC-3' | NdeI site underlined, initiation codon of cgtB<sub>OH4384</sub> in bold |
| SCJ-401 | 5'-CTTAGCGTCGACTTAATGTTTAAAGTTAAAATATTTATT-3' | SalI site underlined, termination codon of cgtB<sub>OH4384</sub> in bold |
| SCJ-402 | 5'-CTTAGCGTCGACTTAAGCTAATAATGTAACCATTAATTTGTT-3' | SalI site underlined, termination codon of cgtB<sub>OH4384</sub> in bold |

FIG. 5B

| | | |
|---|---|---|
| SCJ-403 | 5'-CTTAGCGTCGACTTATTTATTTATATATTGAATATATAGC-3' | SalI site underlined, termination codon of cg1B$_{onssa}$ in bold |
| SCJ-404 | 5'-CTTAGCGTCGACTTAGATTTTTTAAAAAATATTGATTTA-3' | SalI site underlined, termination codon of cg1B$_{us10}$ in bold |
| SCJ-405 | 5'-CTTAGCGTCGACTTAACAAAGAACATTTCGCTTGCTTGATAAT-3' | SalI site underlined, termination codon of cg1B$_{us10}$ in bold |
| SCJ-406 | 5'-CTTAGCGTCGACTTAGTATTTTCAATTAATAAAAATACTCA-3' | SalI site underlined, termination codon of cg1B$_{us10}$ in bold |
| SCJ-408 | 5'-CCCGAATTCCGGTTTTATTTTATATATTGAATATATAGC-3' | EcoRI site underlined, last codon of cg1B$_{onssa}$ in bold |
| SCJ-410 | 5'-CCCGAATTCCGGTTTATTAAAATTTGTTCATATTTCAATAA-3' | EcoRI site underlined, last codon of cg1B$_{1116}$ in bold |
| SCJ-452 | 5'-CCCGAATTCCCCACAAGAACATTTCGCTTGCTTGATAATGAG-3' | EcoRI site underlined, last codon of cg1B$_{us10}$ in bold |
| malE5p | 5'-GAAACAGGATCCATCGATGCTTAGGAGGTCAGATGAAAATCGA-AGAAGGTAAACTGG-3' | BamHI site underlined, the RBS in italicized and underlined; the newly introduced initiation codon is italicized and the first codon of the mature MalE in bold |
| malE3p | 5'-ACGAATCTCTCCACATATGTCCGCCACCCTTGGTGATACGAGT-CTCGC-3' | NdeI site underlined, initiation codon of the gene following malE is in bold |

FIG. 5C

| | | |
|---|---|---|
| malE3p SalI | 5'-GGGGGGGGGGGTCGACTTATTACTGGTGATACGAGTTTGCGCGTCTTC-3' | SalI site underlined, termination codon of malE in bold |
| malE5p EcoRI | 5'-GGGGGGGGGGGGAATTCAAAATCGAAGAAGTTAAATGGTAATCTGC-3' | EcoRI site underlined, first coding codon of the mature MalE in bold |

SEQUENCE LISTING

<160> NUMBER OF SEQ ID NOS: 35

<210> SEQ ID NO 1
<211> LENGTH: 906
<212> TYPE: DNA
<213> ORGANISM: Campylobacter jejuni

<400> SEQUENCE: 1

```
atgtttaaaa tttcaatcat cttaccaact tataatgtgg aacaatatat agcaagggca     60
atagaaagct gtatcaatca gactttaaa gatatagaaa taattgtagt tgatgattgt    120
ggaaatgata atagtataaa tatagccaaa gaatactcta aaaaagacaa aagaataaaa    180
ataatccaca atgaaaaaaa cttaggtctt ttaagagcaa gatatgaagg tgtgaaagta    240
gcaaactctc cttatataat gttttttagat cctgatgatt atttggaact aaatgcttgt    300
gaagagtgta taaaaatttt agatgaacag gatgaagttg atttagtgtt tttcaatgct    360
attgttgaaa gtaatgttat ttcatataaa aagtttgact taattctgg tttttatagc    420
aaaaaagagt ttgtaaaaaa aattattgca agaaaaatt tatattggac tatgtggggg    480
aaacttataa gaaagaaatt gtatttagaa gcttttgcga gtttaagact cgagaaagat    540
gttaaaatca atatggctga agatgtattg ttatattatc caatgttaag tcaagctcaa    600
aaaatagcat atatgaactg taatttatat cattacgtgc ctaataataa ttcaatttgt    660
aatactaaga atgaagtgct tgttaaaaat aatattcaag agttgcagtt ggttttaaac    720
tatttaaggc aaaattatat tttaaacaag tattgtagcg ttctctatgt gctaattaaa    780
tatttgctat atattcaaat atataaaata aaaagaacaa aattaatggt tacattatta    840
gctaaaataa atattttaac tttaaaaatt ttatttaaat ataaaaaatt tttaaaacaa    900
tgttaa                                                                906
```

<210> SEQ ID NO 2
<211> LENGTH: 301
<212> TYPE: PRT
<213> ORGANISM: Campylobacter jejuni

<400> SEQUENCE: 2

```
Met Phe Lys Ile Ser Ile Ile Leu Pro Thr Tyr Asn Val Glu Gln Tyr
1               5                   10                  15

Ile Ala Arg Ala Ile Glu Ser Cys Ile Asn Gln Thr Phe Lys Asp Ile
                20                  25                  30

Glu Ile Ile Val Val Asp Asp Cys Gly Asn Asp Asn Ser Ile Asn Ile
            35                  40                  45
```

```
Ala Lys Glu Tyr Ser Lys Lys Asp Lys Arg Ile Lys Ile Ile His Asn
         50                  55                  60

Glu Lys Asn Leu Gly Leu Leu Arg Ala Arg Tyr Glu Gly Val Lys Val
 65                  70                  75                  80

Ala Asn Ser Pro Tyr Ile Met Phe Leu Asp Pro Asp Asp Tyr Leu Glu
                 85                  90                  95

Leu Asn Ala Cys Glu Glu Cys Ile Lys Ile Leu Asp Glu Gln Asp Glu
            100                 105                 110

Val Asp Leu Val Phe Phe Asn Ala Ile Val Glu Ser Asn Val Ile Ser
             115                 120                 125

Tyr Lys Lys Phe Asp Phe Asn Ser Gly Phe Tyr Ser Lys Lys Glu Phe
         130                 135                 140

Val Lys Lys Ile Ile Ala Lys Lys Asn Leu Tyr Trp Thr Met Trp Gly
145                 150                 155                 160

Lys Leu Ile Arg Lys Lys Leu Tyr Leu Glu Ala Phe Ala Ser Leu Arg
                 165                 170                 175

Leu Glu Lys Asp Val Lys Ile Asn Met Ala Glu Asp Val Leu Leu Tyr
             180                 185                 190

Tyr Pro Met Leu Ser Gln Ala Gln Lys Ile Ala Tyr Met Asn Cys Asn
             195                 200                 205

Leu Tyr His Tyr Val Pro Asn Asn Asn Ser Ile Cys Asn Thr Lys Asn
         210                 215                 220

Glu Val Leu Val Lys Asn Asn Ile Gln Glu Leu Gln Leu Val Leu Asn
225                 230                 235                 240

Tyr Leu Arg Gln Asn Tyr Ile Leu Asn Lys Tyr Cys Ser Val Leu Tyr
                 245                 250                 255

Val Leu Ile Lys Tyr Leu Leu Tyr Ile Gln Ile Tyr Lys Ile Lys Arg
             260                 265                 270

Thr Lys Leu Met Val Thr Leu Leu Ala Lys Ile Asn Ile Leu Thr Leu
             275                 280                 285

Lys Ile Leu Phe Lys Tyr Lys Lys Phe Leu Lys Gln Cys
         290                 295                 300

<210> SEQ ID NO 3
<211> LENGTH: 906
<212> TYPE: DNA
<213> ORGANISM: Campylobacter jejuni

<400> SEQUENCE: 3
atgtttaaaa tttcaatcat cttaccaact tataatgtgg aacaatatat agcaagggca      60
atagaaagct gtatcaatca gacttttaaa gatatagaaa taattgtagt tgatgattgt     120
ggaaatgata atagtataaa tatagccaaa gaatactcta aaaaagacaa agaataaaa      180 ataatcccaca tgaaaaaaa cttaggtctt ttaagagcaa gatatgaagg tgtgaaagta     240
gcaaactctc cttatataat gttttagat cctgatgatt atttggaact aaatgcttgt     300
gaagagtgta taaaaatttt agatgaacag gatgaagttg atttagtgtt tttcaatgct     360
attgttgaaa gtaatgttat ttcatataaa agtttgact ttaattctgg tttttatagc     420
aaaaaagagt ttgtgaaaaa aattattgca agaaaaatt tatattggac tatgtgggg      480 aaacttataa gaagaaatt gtatttagaa gcttttgcga gttaaaaact cgagaaagat     540
gttaaaatca atatggctga agatgtattg ttatattatc caatgttaag tcaagctcaa     600
aaaatagcat atatgaactg taattttat cattacgtgc ctaataataa ttcaatttgt     660
aatactaaga atgaagtgct tgttaaaaat aatattcaag agttgcagtt ggttttaaac    720
```

```
tatttaaggc aaaattatat tttaaacaag tattgtagcg ttctctatgt gctaattaaa      780
tatttgctat atattcaaat atataaaata aaaagaacaa aattaatggt tacattgtta      840
gctaaaataa atattttaac tttaaaaatt ttatttaaat ataaaaaatt tttaaaacaa      900
tgttaa                                                                 906
```

<210> SEQ ID NO 4
<211> LENGTH: 301
<212> TYPE: PRT
<213> ORGANISM: Campylobacter jejuni

<400> SEQUENCE: 4

```
Met Phe Lys Ile Ser Ile Ile Leu Pro Thr Tyr Asn Val Glu Gln Tyr
1               5                   10                  15

Ile Ala Arg Ala Ile Glu Ser Cys Ile Asn Gln Thr Phe Lys Asp Ile
            20                  25                  30

Glu Ile Ile Val Val Asp Asp Cys Gly Asn Asp Asn Ser Ile Asn Ile
        35                  40                  45

Ala Lys Glu Tyr Ser Lys Lys Asp Lys Arg Ile Lys Ile Ile His Asn
    50                  55                  60

Glu Lys Asn Leu Gly Leu Leu Arg Ala Arg Tyr Glu Gly Val Lys Val
65                  70                  75                  80

Ala Asn Ser Pro Tyr Ile Met Phe Leu Asp Pro Asp Asp Tyr Leu Glu
                85                  90                  95

Leu Asn Ala Cys Glu Glu Cys Ile Lys Ile Leu Asp Glu Gln Asp Glu
            100                 105                 110

Val Asp Leu Val Phe Phe Asn Ala Ile Val Glu Ser Asn Val Ile Ser
        115                 120                 125

Tyr Lys Lys Phe Asp Phe Asn Ser Gly Phe Tyr Ser Lys Lys Glu Phe
    130                 135                 140

Val Lys Lys Ile Ile Ala Lys Lys Asn Leu Tyr Trp Thr Met Trp Gly
145                 150                 155                 160

Lys Leu Ile Arg Lys Lys Leu Tyr Leu Glu Ala Phe Ala Ser Leu Lys
                165                 170                 175

Leu Glu Lys Asp Val Lys Ile Asn Met Ala Glu Asp Val Leu Leu Tyr
            180                 185                 190

Tyr Pro Met Leu Ser Gln Ala Gln Lys Ile Ala Tyr Met Asn Cys Asn
        195                 200                 205

Leu Tyr His Tyr Val Pro Asn Asn Ser Ile Cys Asn Thr Lys Asn
    210                 215                 220

Glu Val Leu Val Lys Asn Asn Ile Gln Glu Leu Gln Leu Val Leu Asn
225                 230                 235                 240

Tyr Leu Arg Gln Asn Tyr Ile Leu Asn Lys Tyr Cys Ser Val Leu Tyr
                245                 250                 255

Val Leu Ile Lys Tyr Leu Leu Tyr Ile Gln Ile Tyr Lys Ile Lys Arg
            260                 265                 270

Thr Lys Leu Met Val Thr Leu Leu Ala Lys Ile Asn Ile Leu Thr Leu
        275                 280                 285

Lys Ile Leu Phe Lys Tyr Lys Lys Phe Leu Lys Gln Cys
    290                 295                 300
```

<210> SEQ ID NO 5
<211> LENGTH: 906
<212> TYPE: DNA
<213> ORGANISM: Campylobacter jejuni

<400> SEQUENCE: 5

```
atgtttaaaa tttcaatcat cttaccaact tataatgtgg aacaatatat agcaagggca    60
atagaaagct gtatcaatca gacttttaaa gatatagaaa taattgtagt tgatgattgt   120
ggaaatgata atagtataaa tatagccaaa gaatactcta aaaaagacaa agaataaaa    180
ataatccaca atgaaaaaaa cttaggtctt ttaagagcaa gatatgaagg tgtgaaagta   240
gcaaactctc cttatataat gttttttagat cctgatgatt atttggaact aaatgcttgt   300
gaagagtgta taaaaatttt agatgaacag gatgaagttg atttagtgtt tttcaatgct   360
attgttgaaa gtaatgttat ttcatataaa aagtttgact ttaattctgg tttttatagc   420
aaaaaagagt ttgtaaaaaa aattattgca ataaaaatt tatattggac tatgtggggg   480
aaacttataa gaaagaaatt gtatttagaa gcttttgcga gtttaagact cgagaaagat   540
gttaaaatca atatggctga agatgtattg ttatattatc caatgttaag tcaagctcaa   600
aaaatagcat atatgaactg taatttatat cattacgtgc ctaataataa ttcaatttgt   660
aatactaaga atgaagtgct tgttaaaaat aatattcaag agttgcagtt ggttttaaac   720
tatttaaggc aaaattatat tttaaacaag tattgtagcg ttctctatgt gctaattaaa   780
tatttgctat atattcaaat atataaaata aaaagaacaa aattaatggt tacattatta   840
gctaaaataa atattttaac tttaaaaatt ttatttaaat ataaaaaatt tttaaaacaa   900
tgttaa                                                              906
```

<210> SEQ ID NO 6
<211> LENGTH: 301
<212> TYPE: PRT
<213> ORGANISM: Campylobacter jejuni

<400> SEQUENCE: 6

```
Met Phe Lys Ile Ser Ile Ile Leu Pro Thr Tyr Asn Val Glu Gln Tyr
1               5                   10                  15

Ile Ala Arg Ala Ile Glu Ser Cys Ile Asn Gln Thr Phe Lys Asp Ile
            20                  25                  30

Glu Ile Ile Val Val Asp Asp Cys Gly Asn Asp Asn Ser Ile Asn Ile
        35                  40                  45

Ala Lys Glu Tyr Ser Lys Lys Asp Lys Arg Ile Lys Ile Ile His Asn
    50                  55                  60

Glu Lys Asn Leu Gly Leu Leu Arg Ala Arg Tyr Glu Gly Val Lys Val
65                  70                  75                  80

Ala Asn Ser Pro Tyr Ile Met Phe Leu Asp Pro Asp Asp Tyr Leu Glu
                85                  90                  95

Leu Asn Ala Cys Glu Glu Cys Ile Lys Ile Leu Asp Glu Gln Asp Glu
            100                 105                 110

Val Asp Leu Val Phe Phe Asn Ala Ile Val Glu Ser Asn Val Ile Ser
        115                 120                 125

Tyr Lys Lys Phe Asp Phe Asn Ser Gly Phe Tyr Ser Lys Lys Glu Phe
    130                 135                 140

Val Lys Lys Ile Ile Ala Asn Lys Asn Leu Tyr Trp Thr Met Trp Gly
145                 150                 155                 160

Lys Leu Ile Arg Lys Lys Leu Tyr Leu Glu Ala Phe Ala Ser Leu Arg
                165                 170                 175

Leu Glu Lys Asp Val Lys Ile Asn Met Ala Glu Asp Val Leu Leu Tyr
            180                 185                 190

Tyr Pro Met Leu Ser Gln Ala Gln Lys Ile Ala Tyr Met Asn Cys Asn
        195                 200                 205
```

```
Leu Tyr His Tyr Val Pro Asn Asn Ser Ile Cys Asn Thr Lys Asn
    210                 215                 220

Glu Val Leu Val Lys Asn Asn Ile Gln Glu Leu Gln Leu Val Leu Asn
225                 230                 235                 240

Tyr Leu Arg Gln Asn Tyr Ile Leu Asn Lys Tyr Cys Ser Val Leu Tyr
                245                 250                 255

Val Leu Ile Lys Tyr Leu Leu Tyr Ile Gln Ile Tyr Lys Ile Lys Arg
            260                 265                 270

Thr Lys Leu Met Val Thr Leu Leu Ala Lys Ile Asn Ile Leu Thr Leu
        275                 280                 285

Lys Ile Leu Phe Lys Tyr Lys Lys Phe Leu Lys Gln Cys
        290                 295                 300

<210> SEQ ID NO 7
<211> LENGTH: 912
<212> TYPE: DNA
<213> ORGANISM: Campylobacter jejuni

<400> SEQUENCE: 7
atgagtcaaa tttccatcat actaccaact tataatgtgg aaaaatatat tgctagagca      60
ttagaaagtt gcattaacca aactttttaaa gatatagaaa tcattgtagt agatgattgt    120
ggtaatgata aaagtataga tatagctaaa gagtatgcta gtaaagatga tagaataaaa    180
atcatacata tgaagagaa tttaaagctt taagagcaa gatatgaagg tgctaaagta     240
gcaacttcac cttatatcat gttttagat tctgatgatt atttagaact taatgcttgc     300
gaagaatgta ttaaaatttt ggatatgggt gggggggta aaattgattt gttgtgtttt     360
gaagctttta ttaccaatgc aaaaaaatca ataaaaaaat taaatataaa acaaggaaaa    420
tacaacaaca aagaatttac aatgcaaata cttaaaacta aaatccatt ttggacaatg     480 tgggctaaaa taatcaaaaa agatatttat ttaaaagcct tcaacatgtt aaatctcaaa    540
aaagaaatca aataaatat ggcagaagat gccttattat attatccttt gacaatatta    600
tctaatgaaa tattttactt aacacaacct ttgtataccc agcatgtaaa tagcaattct    660
ataacaaata atattaattc tttagaagct aatattcaag aacataaaat tgttttaaat   720
gttttaaaat caattaaaaa taaaaaaaca cctctatatt ttctaattat atatttatta   780
aaaattcaat tattgaaata tgaacaaaat tttaataaaa gaaatataaa tcttatttat   840
tataaaataa atattttata tcaaaaatat caattcaaat ggaaaaaatt tttatataat   900
ttaattccgt aa                                                        912

<210> SEQ ID NO 8
<211> LENGTH: 303
<212> TYPE: PRT
<213> ORGANISM: Campylobacter jejuni

<400> SEQUENCE: 8

Met Ser Gln Ile Ser Ile Ile Leu Pro Thr Tyr Asn Val Glu Lys Tyr
1               5                   10                  15

Ile Ala Arg Ala Leu Glu Ser Cys Ile Asn Gln Thr Phe Lys Asp Ile
            20                  25                  30

Glu Ile Ile Val Val Asp Asp Cys Gly Asn Asp Lys Ser Ile Asp Ile
        35                  40                  45

Ala Lys Glu Tyr Ala Ser Lys Asp Asp Arg Ile Lys Ile Ile His Asn
    50                  55                  60

Glu Glu Asn Leu Lys Leu Leu Arg Ala Arg Tyr Glu Gly Ala Lys Val
```

```
             65                  70                  75                  80
Ala Thr Ser Pro Tyr Ile Met Phe Leu Asp Ser Asp Asp Tyr Leu Glu
                     85                  90                  95

Leu Asn Ala Cys Glu Glu Cys Ile Lys Ile Leu Asp Met Gly Gly Gly
                100                 105                 110

Gly Lys Ile Asp Leu Leu Cys Phe Glu Ala Phe Ile Thr Asn Ala Lys
            115                 120                 125

Lys Ser Ile Lys Lys Leu Asn Ile Lys Gln Gly Lys Tyr Asn Asn Lys
        130                 135                 140

Glu Phe Thr Met Gln Ile Leu Lys Thr Lys Asn Pro Phe Trp Thr Met
145                 150                 155                 160

Trp Ala Lys Ile Ile Lys Lys Asp Ile Tyr Leu Lys Ala Phe Asn Met
                    165                 170                 175

Leu Asn Leu Lys Lys Glu Ile Lys Ile Asn Met Ala Glu Asp Ala Leu
                180                 185                 190

Leu Tyr Tyr Pro Leu Thr Ile Leu Ser Asn Glu Ile Phe Tyr Leu Thr
            195                 200                 205

Gln Pro Leu Tyr Thr Gln His Val Asn Ser Asn Ser Ile Thr Asn Asn
        210                 215                 220

Ile Asn Ser Leu Glu Ala Asn Ile Gln Glu His Lys Ile Val Leu Asn
225                 230                 235                 240

Val Leu Lys Ser Ile Lys Asn Lys Lys Thr Pro Leu Tyr Phe Leu Ile
                    245                 250                 255

Ile Tyr Leu Leu Lys Ile Gln Leu Leu Lys Tyr Glu Gln Asn Phe Asn
                260                 265                 270

Lys Arg Asn Ile Asn Leu Ile Tyr Tyr Lys Ile Asn Ile Leu Tyr Gln
            275                 280                 285

Lys Tyr Gln Phe Lys Trp Lys Lys Phe Leu Tyr Asn Leu Ile Pro
        290                 295                 300

<210> SEQ ID NO 9
<211> LENGTH: 894
<212> TYPE: DNA
<213> ORGANISM: Campylobacter jejuni

<400> SEQUENCE: 9
atgtttaaaa tttcaatcat cttgccaact tataatgtgg aacaatatat agcaagggca    60
atagaaagtt gtatcaatca gacttttaaa aatatagaaa taattgtagt tgatgattgt   120
ggaagtgaca aaagtataga tatagttaaa gaatatgcca aaaagatgat agaataaaa    180 atcatacata tgaagaaaaa tttaaaactt ttaagagcta gatatgaagg tgtaaaagta   240
gcaaactctc cttatataat gttttttagat cctgatgatt atttagaact taatgcttgt   300
gaagaatgta tgaaaatttt aaaaaacaat gaaatagatt tattattttt taatgcattt   360
gtattggaaa ataacaataa aatagaaaga aagttgaatt ttcaagaaaa atgttatgta   420 aaaaagatt ttttaaaaga actattaaaa actaaaaatt tattttggac agtgtgggca    480
aaagtcataa aaaagaatt atatctcaag gctgttggtt taatatcgct agaaaatgct    540
aaaataaata tggctgaaga tgttttatta tattacccctt tgataaatat ttcaaatact   600
atatttcact tgagtaaaaa tttatacaat tatcaaataa ataatttctc tataaccaaa   660
acattaacat tgcaaaatat aaaaacaaat atacaagaac aagataatgt tctatatctt   720
ctaaagaaga tgcaatataa ttacaatttt aacttaactt tgcttaaatt aattgagtat   780 ttttattaa ttgaaaaata tcattatca agcaagcgaa atgttctttg ttttaaaatc    840
```
aatatttttt ttaaaaaaat ccaatttaaa ttttatcgct tgctgaagat gtaa            894

<210> SEQ ID NO 10
<211> LENGTH: 297
<212> TYPE: PRT
<213> ORGANISM: Campylobacter jejuni

<400> SEQUENCE: 10

Met Phe Lys Ile Ser Ile Ile Leu Pro Thr Tyr Asn Val Glu Gln Tyr
1               5                   10                  15

Ile Ala Arg Ala Ile Glu Ser Cys Ile Asn Gln Thr Phe Lys Asn Ile
            20                  25                  30

Glu Ile Ile Val Val Asp Asp Cys Gly Ser Asp Lys Ser Ile Asp Ile
        35                  40                  45

Val Lys Glu Tyr Ala Lys Lys Asp Asp Arg Ile Lys Ile Ile His Asn
    50                  55                  60

Glu Glu Asn Leu Lys Leu Leu Arg Ala Arg Tyr Glu Gly Val Lys Val
65                  70                  75                  80

Ala Asn Ser Pro Tyr Ile Met Phe Leu Asp Pro Asp Asp Tyr Leu Glu
                85                  90                  95

Leu Asn Ala Cys Glu Glu Cys Met Lys Ile Leu Lys Asn Asn Glu Ile
            100                 105                 110

Asp Leu Leu Phe Phe Asn Ala Phe Val Leu Glu Asn Asn Asn Lys Ile
        115                 120                 125

Glu Arg Lys Leu Asn Phe Gln Glu Lys Cys Tyr Val Lys Lys Asp Phe
    130                 135                 140

Leu Lys Glu Leu Leu Lys Thr Lys Asn Leu Phe Trp Thr Val Trp Ala
145                 150                 155                 160

Lys Val Ile Lys Lys Glu Leu Tyr Leu Lys Ala Val Gly Leu Ile Ser
                165                 170                 175

Leu Glu Asn Ala Lys Ile Asn Met Ala Glu Asp Val Leu Leu Tyr Tyr
            180                 185                 190

Pro Leu Ile Asn Ile Ser Asn Thr Ile Phe His Leu Ser Lys Asn Leu
        195                 200                 205

Tyr Asn Tyr Gln Ile Asn Asn Phe Ser Ile Thr Lys Thr Leu Thr Leu
    210                 215                 220

Gln Asn Ile Lys Thr Asn Ile Gln Glu Gln Asp Asn Val Leu Tyr Leu
225                 230                 235                 240

Leu Lys Lys Met Gln Tyr Asn Tyr Asn Phe Asn Leu Thr Leu Leu Lys
                245                 250                 255

Leu Ile Glu Tyr Phe Leu Leu Ile Glu Lys Tyr Ser Leu Ser Ser Lys
            260                 265                 270

Arg Asn Val Leu Cys Phe Lys Ile Asn Ile Phe Lys Lys Ile Gln
        275                 280                 285

Phe Lys Phe Tyr Arg Leu Leu Lys Met
    290                 295

<210> SEQ ID NO 11
<211> LENGTH: 39
<212> TYPE: DNA
<213> ORGANISM: Artificial Sequence
<220> FEATURE:
<223> OTHER INFORMATION: Chemically synthesized

<400> SEQUENCE: 11
cttaggaggt catatgttta aaatttcaat catcttacc            39

```
<210> SEQ ID NO 12
<211> LENGTH: 37
<212> TYPE: DNA
<213> ORGANISM: Artificial Sequence
<220> FEATURE:
<223> OTHER INFORMATION: Chemically synthesized

<400> SEQUENCE: 12
cctaggtcga cctctaaaaa aaatattctt aacattg                               37

<210> SEQ ID NO 13
<211> LENGTH: 39
<212> TYPE: DNA
<213> ORGANISM: Artificial Sequence
<220> FEATURE:
<223> OTHER INFORMATION: Chemically synthesized

<400> SEQUENCE: 13
cttaggaggt catatgagtc aaatttccat catactacc                             39

<210> SEQ ID NO 14
<211> LENGTH: 43
<212> TYPE: DNA
<213> ORGANISM: Artificial Sequence
<220> FEATURE:
<223> OTHER INFORMATION: Chemically synthesized

<400> SEQUENCE: 14
cctaggtcga cttacggaat taaattatat aaaaattttt tcc                        43

<210> SEQ ID NO 15
<211> LENGTH: 38
<212> TYPE: DNA
<213> ORGANISM: Artificial Sequence
<220> FEATURE:
<223> OTHER INFORMATION: Chemically synthesized

<400> SEQUENCE: 15
gctgctggac atatgtttaa aatttcaatc atcttgcc                              38

<210> SEQ ID NO 16
<211> LENGTH: 48
<212> TYPE: DNA
<213> ORGANISM: Artificial Sequence
<220> FEATURE:
<223> OTHER INFORMATION: Chemically synthesized

<400> SEQUENCE: 16
cttagcgtcg acttattaca tcttcagcaa gcgataaaat ttaaattg                   48

<210> SEQ ID NO 17
<211> LENGTH: 41
<212> TYPE: DNA
<213> ORGANISM: Artificial Sequence
<220> FEATURE:
<223> OTHER INFORMATION: Chemically synthesized

<400> SEQUENCE: 17
gctgctggac atatgagtca aatttccatc atactaccaa c                          41

<210> SEQ ID NO 18
<211> LENGTH: 42
<212> TYPE: DNA
<213> ORGANISM: Artificial Sequence
<220> FEATURE:
<223> OTHER INFORMATION: Chemically synthesized

<400> SEQUENCE: 18
```
cttagcgtcg acttaacatt gttttaaaaa tttttatat tt                                42

<210> SEQ ID NO 19
<211> LENGTH: 45
<212> TYPE: DNA
<213> ORGANISM: Artificial Sequence
<220> FEATURE:
<223> OTHER INFORMATION: Chemically synthesized

<400> SEQUENCE: 19
cttagcgtcg acttatttga attgagattt ttgatataaa atatt                           45

<210> SEQ ID NO 20
<211> LENGTH: 45
<212> TYPE: DNA
<213> ORGANISM: Artificial Sequence
<220> FEATURE:
<223> OTHER INFORMATION: Chemically synthesized

<400> SEQUENCE: 20
cttagcgtcg acttatattt tataataaat aagatttata tttct                           45

<210> SEQ ID NO 21
<211> LENGTH: 45
<212> TYPE: DNA
<213> ORGANISM: Artificial Sequence
<220> FEATURE:
<223> OTHER INFORMATION: Chemically synthesized

<400> SEQUENCE: 21
cttagcgtcg acttatttat taaaattttg ttcatatttc aataa                           45

<210> SEQ ID NO 22
<211> LENGTH: 41
<212> TYPE: DNA
<213> ORGANISM: Artificial Sequence
<220> FEATURE:
<223> OTHER INFORMATION: Chemically synthesized

<400> SEQUENCE: 22
gctgctggac atatgtttaa aatttcaatc atcttaccaa c                               41

<210> SEQ ID NO 23
<211> LENGTH: 43
<212> TYPE: DNA
<213> ORGANISM: Artificial Sequence
<220> FEATURE:
<223> OTHER INFORMATION: Chemically synthesized

<400> SEQUENCE: 23
cttagcgctg acttataaaa ttttaaagt taaatatttt att                              43

<210> SEQ ID NO 24
<211> LENGTH: 43
<212> TYPE: DNA
<213> ORGANISM: Artificial Sequence
<220> FEATURE:
<223> OTHER INFORMATION: Chemically synthesized

<400> SEQUENCE: 24
cttagcgtcg acttaagcta ataatgtaac cattaatttt gtt                             43

<210> SEQ ID NO 25
<211> LENGTH: 43
<212> TYPE: DNA
<213> ORGANISM: Artificial Sequence

```
<220> FEATURE:
<223> OTHER INFORMATION: Chemically sythesized

<400> SEQUENCE: 25
cttagcgtcg acttatttta ttttatatat ttgaatatat agc          43

<210> SEQ ID NO 26
<211> LENGTH: 43
<212> TYPE: DNA
<213> ORGANISM: Artificial Sequence
<220> FEATURE:
<223> OTHER INFORMATION: Chemically synthesized

<400> SEQUENCE: 26
cttagcgtcg acttagattt ttttaaaaaa aatattgatt tta          43

<210> SEQ ID NO 27
<211> LENGTH: 43
<212> TYPE: DNA
<213> ORGANISM: Artificial Sequence
<220> FEATURE:
<223> OTHER INFORMATION: Chemically synthesized

<400> SEQUENCE: 27
cttagcgtcg acttaacaaa gaacatttcg cttgcttgat aat          43

<210> SEQ ID NO 28
<211> LENGTH: 43
<212> TYPE: DNA
<213> ORGANISM: Artificial Sequence
<220> FEATURE:
<223> OTHER INFORMATION: Chemically synthesized

<400> SEQUENCE: 28
cttagcgtcg acttagtatt tttcaattaa taaaaaatac tca          43

<210> SEQ ID NO 29
<211> LENGTH: 40
<212> TYPE: DNA
<213> ORGANISM: Artificial Sequence
<220> FEATURE:
<223> OTHER INFORMATION: Chemically synthesized

<400> SEQUENCE: 29
ccggaattcc ggttttattt tatatatttg aatatatagc              40

<210> SEQ ID NO 30
<211> LENGTH: 42
<212> TYPE: DNA
<213> ORGANISM: Artificial Sequence
<220> FEATURE:
<223> OTHER INFORMATION: Chemically synthesized

<400> SEQUENCE: 30
ccggaattcc ggtttattaa aattttgttc atatttcaat aa           42

<210> SEQ ID NO 31
<211> LENGTH: 43
<212> TYPE: DNA
<213> ORGANISM: Artificial Sequence
<220> FEATURE:
<223> OTHER INFORMATION: Chemically synthesized

<400> SEQUENCE: 31
ccggaattcg ccacaaagaa catttcgctt gcttgataat gag          43
```

```
<210> SEQ ID NO 32
<211> LENGTH: 57
<212> TYPE: DNA
<213> ORGANISM: Artificial Sequence
<220> FEATURE:
<223> OTHER INFORMATION: Chemically synthesized

<400> SEQUENCE: 32
gaaacaggat ccatcgatgc ttaggaggtc agatgaaaat cgaagaaggt aaactgg      57

<210> SEQ ID NO 33
<211> LENGTH: 48
<212> TYPE: DNA
<213> ORGANISM: Artificial Sequence
<220> FEATURE:
<223> OTHER INFORMATION: Chemically synthesized

<400> SEQUENCE: 33
acgaatcctc cacatatgtc cgccacccctt ggtgatacga gtctgcgc               48

<210> SEQ ID NO 34
<211> LENGTH: 48
<212> TYPE: DNA
<213> ORGANISM: Artificial Sequence
<220> FEATURE:
<223> OTHER INFORMATION: Chemically synthesized

<400> SEQUENCE: 34
gggggggggg tcgacttatt acttggtgat acgagtctgc gcgtcttc                48

<210> SEQ ID NO 35
<211> LENGTH: 45
<212> TYPE: DNA
<213> ORGANISM: Artificial Sequence
<220> FEATURE:
<223> OTHER INFORMATION: Chemically synthesized

<400> SEQUENCE: 35
gggggggggg aattcaaaat cgaagaaggt aaactggtaa tctgc                   45
```

ENGINEERED VERSIONS OF CGTB (β-1,3 GALACTOSYLTRANSFERASE) ENZYMES, WITH ENHANCED ENZYMATIC PROPERTIES

CROSS-REFERENCES TO RELATED APPLICATIONS

This application is a National Phase application of the International Appl. No. PCT/CA2008/000738 filed Apr. 18, 2008, which claims the benefit of U.S. Provisional Application No. 60/925,451, filed Apr. 20, 2007, which is herein incorporated by reference for all purposes.

FIELD OF THE INVENTION

The present invention provides CgtB proteins with enhanced β1,3-galactosaminyltransferase activity, nucleic acids that encode the CgtB proteins and methods for use of the CgtB proteins.

BACKGROUND OF THE INVENTION

The cell surface glycolipids (lipooligosaccharides, LOS) of *Campylobacter jejuni* show considerable structural diversity, with many ganglioside mimics being found in pathogenic strains and this has been correlated to the genetic diversity of the locus (Gilbert, M. et al., *J Biol. Chem.* 277:327-337 (2002)). The LOS biosynthesis gene clusters of a large number of *C. jejuni* strains have been examined and have been divided in eight classes ("A" to "H") based on their gene content and genetic organization (Parker, C. T. et al., *J Clin Microbiol.* 43:2771-2781 (2005)). The first three classes ("A", "B" and "C") contain the neuBCA and cst-II genes needed for the biosynthesis of sialic acid and its incorporation into the growing LOS to constitute ganglioside mimics (Gilbert, M. et al., *J Biol. Chem.* 277:327-337 (2002); Parker, C. T. et al., *J Clin Microbiol.* 43:2771-2781 (2005)). As we are interested in the synthesis of sialylated glycans, we have focused our research efforts on the enzymes encoded by genes from clusters belonging to classes "A", "B" and "C" (described in Gilbert, M. et al., *J Biol. Chem.* 277:327-337 (2002)).

There exists considerable amino acid sequence variation between *C. jejuni* strains for the same LOS biosynthesis glycosyltransferase (Gilbert, M. et al., *J Biol. Chem.* 277:327-337 (2002)). The investigation of the LOS biosynthesis gene clusters from eleven *C. jejuni* strains expressing eight different serotypes led to the identification of five distinct mechanisms by which this bacterium can vary the structure of its LOS (Gilbert, M. et al., *J Biol. Chem.* 277:327-337 (2002)). One of these mechanisms consists in the occurrence of single or multiple mutations leading to "allelic" glycosyltransferases with different acceptor specificities (Gilbert, M. et al., *J Biol. Chem.* 277:327-337 (2002)). This was clearly illustrated by the investigation of variants of CgtA (β1,4-N-acetylgalactosaminyltransferase) and of Cst-II (α-2,3-/2,8-sialyltransferase). Six CgtA variants (sharing 34% overall amino acid sequence identity) from classes "A", "B" and "C" displayed different specific activities towards non-sialylated (lactose), mono ($GM3^1$)- or disialylated ($GD3^1$) FCHASE-labeled acceptors (Gilbert, M. et al., *J Biol. Chem.* 277:327-337 (2002)). Similarly, six variants of Cst-II (sharing 92% overall amino acid sequence identity) from classes "A" and "B" displayed different specific activities towards non-sialylated (lactose) or sialylated ($GM3^1$) FCHASE-labeled acceptors (Gilbert, M. et al., *J Biol. Chem.* 277:327-337 (2002)). A Cst-II variant belonging to class "C" had previously been shown to be active with lactose-FCHASE and inactive with GM3-FCHASE (Gilbert, M et al., *J Biol. Chem.* 275:3896-3906 (2000)). These differences in acceptor preference and in specific activity levels are a consequence of amino acid sequence divergence between enzyme variants.

As is the case for CgtA, CgtB (β1,3-galactosaminyltransferase) enzymes exhibit sequence divergence: only 47% amino acid sequence identity has been reported between the sequences from eleven strains belonging to classes "A", "B" and "C" (Gilbert, M. et al., *J Biol. Chem.* 277:327-337 (2002)). The activity and acceptor preference of CgtB variants from classes "A", "B" and "C" had not been determined, however, as has been done for CgtA and Cst-II (Gilbert, M et al., *J Biol. Chem.* 275:3896-3906 (2000); Gilbert, M. et al., *J Biol. Chem.* 277:327-337 (2002)).

The CgtB sequences from strains ATCC 43432 (SEQ ID NOs: 3 and 4), OH4384 (SEQ ID NOs: 1 and 2) and ATCC 43460 (SEQ IDs: 5 and 6) (serotypes HS:4, HS:19 and HS:41, respectively; all members of class "A") share 99% sequence identity (Gilbert, M. et al., *J Biol. Chem.* 277:327-337 (2002)). CgtB from strain OH4384 (SEQ ID NOs: 7 and 8) ($CgtB_{OH4384}$, also of serotype HS:19; FIG. 1A) was chosen for further characterization since it had already been partially characterized (Gilbert, M et al., *J Biol. Chem.* 275:3896-3906 (2000)). CgtB from strain NCTC 11168 (SEQ ID NOs: 7 and 8) ($CgtB_{11168}$; serotype HS:2; FIG. 1B), a member of the class "C" group was also chosen as it has been used for the in vitro synthesis of the glycone moiety of ganglioside $GM_1a$ and for the synthesis of ganglioside mimics (Linton, D. et al., *Mol. Microbiol.* 37:501-14 (2000); Blixt, O. et al., *Carbohydrate Res.* 340:1963-1972 (2005)). A second member of class "A", that from strain ATCC 43438 (SEQ ID NOs: 9 and 10) ($CgtB_{HS:10}$; serotype HS:10), was included for the comparison because its sequence differs from those of the other members of class "A". Compared to the other members of its class, the carboxy-terminal of $CgtB_{HS:10}$ contains a large number of amino acid substitutions (Gilbert, M. et al., *J Biol. Chem.* 277:327-337 (2002)). These changes may reflect acceptor preferences (FIG. 1C; Gilbert, M. et al., *J Biol Chem.* 277:327-337 (2002)). No CgtB variant from class "B" was chosen, as their amino acid sequences are not distinct from those of class "A" (Gilbert, M. et al., *J Biol. Chem.* 277:327-337 (2002)).

Bacterial glycosyltransferases have been successfully incorporated in various chemo-enzymatic schemes. Improved enzymatic activities could increase the use of bacterial glycosyltransferases in production of oligosaccharides including glycoproteins, glycopeptides, glycolipids, and gangliosides.

BRIEF SUMMARY OF THE INVENTION

In one aspect, the present invention provides a β-1,3-galactosyltransferase polypeptide including a truncated CgtB polypeptide with 1 to 35 amino acids removed from the C-terminal end of the CgtB polypeptide and a maltose binding protein fused to the C-terminal domain of the CgtB polypeptide. The β-1,3-galactosyltransferase polypeptide of the present invention transfers a galactose moiety from a donor substrate to an acceptor substrate.

In some embodiments of the present invention, the β-1,3-galactosyltransferase polypeptide is from *Campylobacter jejuni* OH4384. In other embodiments, the β-1,3-galactosyltransferase polypeptide of the present invention is from *Campylobacter jejuni* NCTC11168. In some embodiments, the β-1,3-galactosyltransferase polypeptide of the present invention is from *Campylobacter jejuni* HS:10.

In some aspects, the CgtB polypeptide of the present invention shares 90%, 91%, 92%, 93%, 94%, 95%, 96%, 97%, 98%, 99%, or 100% identity with an amino acid sequence selected from the group consisting of SEQ ID NO:2, SEQ ID NO:4, SEQ ID NO:6, SEQ ID NO:8, and SEQ ID NO:10.

In some embodiments the acceptor substrate for the β-1,3-galactosyltransferase is a saccharide, oligosaccharide, glycopeptide, glycoprotein, glycolipid, ganglioside, or a ganglioside headgroup.

In one aspect the β-1,3-galactosyltransferase of the present invention has an amino acid sequence that is 90%, 91%, 92%, 93%, 94%, 95%, 96%, 97%, 98%, 99%, or 100% identical to amino acids 1-266 of SEQ ID NO:2. In another aspect the β-1,3-galactosyltransferase of the present invention has an amino acid sequence that is 90%, 91%, 92%, 93%, 94%, 95%, 96%, 97%, 98%, 99%, or 100% identical to amino acids 1-271 of SEQ ID NO:2. The truncated CgtB polypeptide with 90%, 91%, 92%, 93%, 94%, 95%, 96%, 97%, 98%, 99%, or 100% identity with amino acids 1-266 of SEQ ID NO:2 can be derived from *Campylobacter jejuni* OH4383, or OH4382 or O:4, or O:19 or O:36, or O:41 or HB93-13.

In one embodiment, the CgtB β-1,3-galactosyltransferase polypeptide of the present invention shares at least 91% identity with amino acid residues 1-271 of SEQ ID NO:2. In another embodiment, the CgtB β-1,3-galactosyltransferase polypeptide comprises amino acid residues 1-271 of SEQ ID NO:2. In a further embodiment the CgtB β-1,3-galactosyltransferase polypeptide comprises amino acid residues 1-271 of SEQ ID NO:2 and an MBP domain fused to the C-terminus of the protein.

In some embodiments, the present invention provides a method for producing a galactosylated product saccharide involving contacting an acceptor substrate with the β-1,3-galactosyltransferase polypeptide (truncated CgtB protein) and a donor substrate comprising galactose, thus allowing transfer of the galactose moiety to the acceptor saccharide to occur resulting in a galactosylated product saccharide.

In other embodiments, the present invention provides a method for producing a glactosylated product protein or peptide involving contacting an acceptor substrate with the β-1,3-galactosyltransferase polypeptide (truncated CgtB protein) and a donor substrate comprising galactose, thus allowing transfer of the galactose moiety to the acceptor saccharide to occur resulting in a galactosylated product protein or peptide.

In some embodiments, the present invention provides a method for producing a glactosylated product glycolipid or ganglioside involving contacting an acceptor substrate with the β-1,3-galactosyltransferase polypeptide (truncated CgtB protein) and a donor substrate comprising galactose, thus allowing transfer of the galactose moiety to the acceptor saccharide to occur resulting in a galactosylated product glycolipid or ganglioside.

In one aspect, the present invention provides a truncated CgtB polypeptide with about 1 to about 35 amino acids removed from its C-terminal end which has a function of transferring a galacose moiety from a donor substrate to an acceptor substrate. In some aspects, the CgtB polypeptide of the present invention is selected from the group consisting of SEQ ID NO:2, SEQ ID NO:4, SEQ ID NO:6, SEQ ID NO:8, and SEQ ID NO:10.

BRIEF DESCRIPTION OF THE DRAWINGS

FIG. 1 depicts the core oligosaccharides from three *Campylobacter jejuni* strains. (A) strain OH4384 (Aspinall, G. O. et al., *Biochemistry.* 33:241-249 (1994)). (B) strain NCTC 11168 (Szymanski, C. M. et al., *J Biol. Chem.* 278: 24509-24520 (2003)) with the phase variable terminal Gal residue (St-Michael, F. et al., *Eur J Biochem.* 269:5119-5136 (2002)) in italics. (C) strain ATCC 43438 (Nam, Shin J. E. et al., *Carbohydrate Res.* 305:223-232 (1997)). In all cases, the galactosyl residue added by CgtB is in bold type and the branched sialic acid residue important for acceptor preference is boxed.

FIG. 2A illustrates multiple sequence alignment of representative CgtB enzyme variants. OH4384 is $CgtB_{O4384}$ [SEQ ID NO:2], 11168 is $CgtB_{11168}$ [SEQ ID NO:8], HS:10 is $CgtB_{HS:10}$ [SEQ ID NO:10]. Identical amino acid residues in all three sequences are white on a black background; those identical between any two sequences are white on a gray background. This alignment was made using ClustalX (Nicholas, K. B. et al., GeneDoc: Analysis and visualization of genetic variation. EMBNEW.NEWS. 4: 14 (www.psc.edu/biomed/genedoc) (1997)) and was reformatted in GeneDoc (Thompson, J. D. et al., *Nucleic Acids Res.* 25:4876 4882 (1997)). FIG. 2B shows the percentages of identity and similarity between any two CgtB variants as assigned in Genedoc.

FIG. 5A, 5B and 5C depicts the oligonucleotide primers used for this work,: CJ-300 [SEQ ID NO:16]; SCJ-301 [SEQ ID NO:15]; SCJ-319 [SEQ ID NO:17]; SCJ-322 [SEQ ID NO:18]; SCJ-368 [SEQ ID NO:19]; SCJ-369 [SEQ ID NO:20]; SCJ-370 [SEQ ID NO:21]; SCJ-400 [SEQ ID NO:22]; SCJ-401 [SEQ ID NO:23]; SCJ-402 [SEQ ID NO:24]; SCJ-403 [SEQ ID NO:25]; SCJ-404 [SEQ ID NO:26]; SCJ-405 [SEQ ID NO:27]; SCJ-406 [SEQ ID NO:28]; SCJ-408 [SEQ ID NO:29]; SCJ-410 [SEQ ID NO:30]; SCJ-452 [SEQ ID NO:31]; malE5p [SEQ ID NO:32]; malE3p [SEQ ID NO:33]: male3p SalI [SEQ ID NO:34]; malE5p ecoRI [SEQ ID NO: 35].

DETAILED DESCRIPTION OF THE INVENTION

I. Introduction

Figure 3:
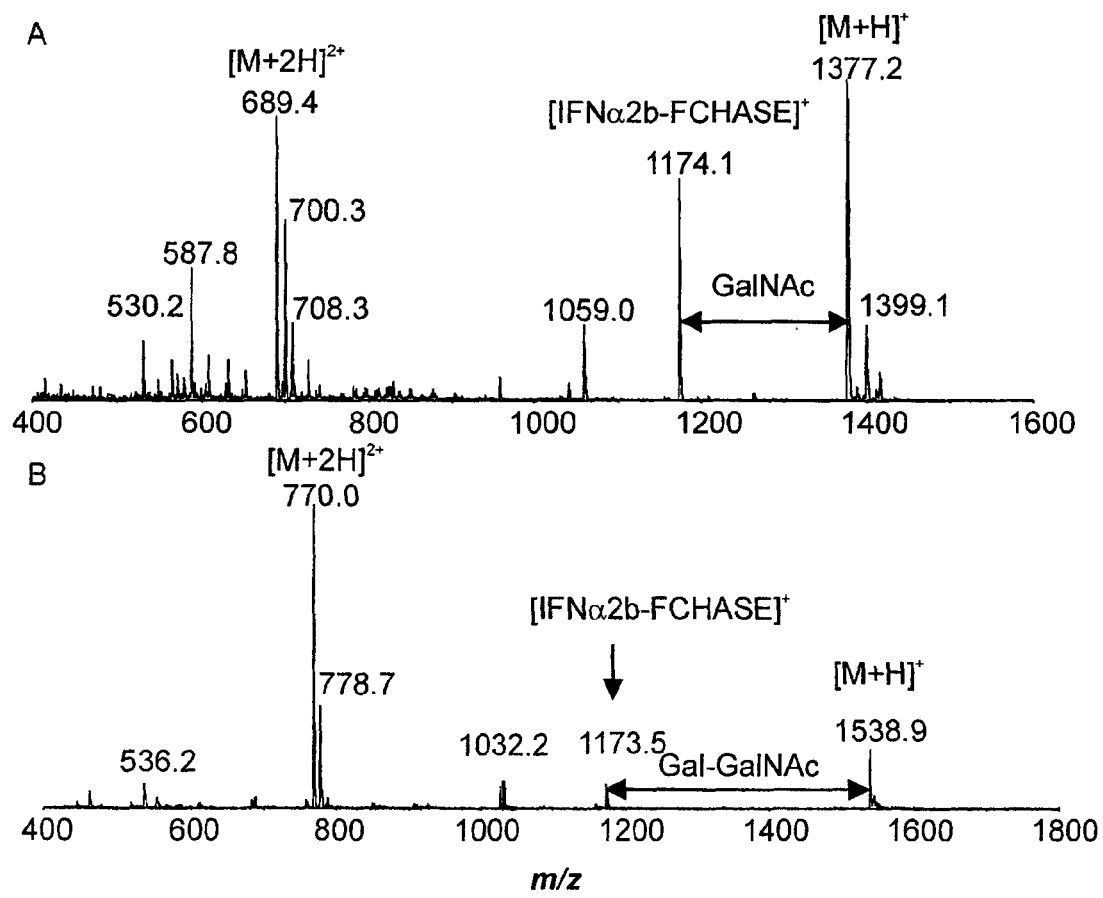
FIG. 3A depicts the results of a CE-MS analysis of IFNα2b [Tn]-FCHASE.
FIG. 3B depicts the results of a CE-MS analysis of IFNα2b[T-Ag]-FCHASE. Relevant species are identified on the mass spectrograph; see the main text for details.

This invention provides for the first time C-terminally truncated CgtB proteins with enhanced enzymatic activity. The invention also provides disclosure of preferred acceptors for certain CgtB proteins and methods to use the CgtB proteins.

Exemplary C-terminally truncated CgtB proteins include, e.g., CgtB from *C. jejuni* OH4383 ($CgtB_{OH4384}$), CgtB from *C. jejuni* NCTC11168 ($CgtB_{11168}$), and CgtB from *C. jejuni* HS:10 ($CgtB_{HS10}$). Further enhancement of enzymatic activity was observed when a maltose binding protein (MBP)

domain was fused to the C-terminus of C-terminally truncated CgtB$_{OH4384}$, CgtB$_{11168}$, or CgtB$_{HS10}$ proteins.

II. Definitions

The following abbreviations are used herein:

Ara=arabinosyl;

Fru=fructosyl;

Fuc=fucosyl;

Gal=galactosyl;

GalNAc=N-acetylgalactosaminyl;

Glc=glucosyl;

GlcNAc=N-acetylglucosaminyl;

Man=mannosyl; and

NeuAc=sialyl (N-acetylneuraminyl).

An "acceptor substrate" or an "acceptor saccharide" for a glycosyltransferase, e.g., a CgtB polypeptide, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for β-1,3-glycosyltransferases, e.g., CgtB from *C. jejuni* strains OH4383, NCTC11168, and HS:10, and additional glycosyltransferases, are described herein. In some embodiments, a CgtB acceptor substrate has a terminal galactose residue. In some embodiments, a CgtB acceptor substrate has an N-acetylgalactosaminyl residue. Labeled CgtB acceptor substrates include, e.g., GalNAcβ-1,4-Galβ-1,4-Glc-FCHASE, GalNAcβ-1,4-[NeuAcα-2,3]-Galβ-1,4-Glc-FCHASE, GalNAcβ-1,4-[NeuAc-α-2,3]-Galβ-1,4-Glc-sphingosine-FCHASE, GalNAcβ-1,4-[NeuAcα-2,8-NeuAcα-2,3]-Galβ-1,4-Glc-FCHASE, GalNAcβ-FCHASE, GalNAc-α-FCHASE, GalNAc-β-p-Nitrophenyl, GalNAc-α-p-Nitrophenyl, FCHASE-NH-Val-Gly-Val-Thr[GalNAc-α-]Glu-Thr-Pro-COOH, IFNα2b[Thr-134-GalNAc]. Truncated CgtB proteins can also be used to add galactose residues to unlabeled acceptor substrates with, e.g., the structures listed above. Unlabeled acceptor substrates are used, e.g., to make galactosylated products on a commercial scale.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for CgtE proteins include, e.g., UDP-GalNAc or UDP-Gal. Donor substrates for sialyltransferases, for example, are activated sugar nucleotides comprising the desired sialic acid. The donor substrate for CgtB is UDP-Gal. For instance, in the case of NeuAc, the activated sugar is CMP-NeuAc. Bacterial, plant, and fungal systems can sometimes use other activated nucleotide sugars. Donor substrates for CgtB proteins include, e.g., UDP-Gal.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3,2→3, or (2,3). Each saccharide is a pyranose or furanose.

As used herein, a "galactose moiety" refers to a molecule that includes galactose or that can be derived from galactose. Galactose moieties are usually monosaccharides, e.g., galactose.

As used herein, a "galactosylated product saccharide" refers an oligosaccharide, a polysaccharide, or a carbohydrate moiety, either unconjugated or conjugated to a glycolipid or a glycoprotein, e.g., a biomolecule, that includes a galactose moiety. Any of the above galactose moieties can be used, e.g., galactose. In preferred embodiments the galactose moiety transferred by CgtB is UDP-Gal.

A "poly-galactosylated product saccharide" refers an oligosaccharide, a polysaccharide, or a carbohydrate moiety, either unconjugated or conjugated to a glycolipid or a glycoprotein, e.g., a biomolecule, that includes a polymer of galactose residues, e.g., a polymer of two or more galactose residues. In some embodiments the products formed by C-terminally-truncated CgtB proteins (with or without a C-terminal MBP domain), have less than 1%, 2%, 3%, 4%, 5%, 6%, 7%, 8%, 9%, 10%, 15%, 20%, 25%, 30%, 40%, 50%, 60%, 70%, 80%, or 90% poly-galactosylated product saccharides.

In some embodiments other sugar moieties, e.g., fucose, sialic acid, glucose, GalNAc or GlcNAc, are also added to the acceptor substrate through the action of additional glycosyltransferases to produce the galactosylated product saccharide. In some embodiments, the acceptor substrate comprises a galactose moiety and the CgtB protein is used to add an additional galactose moiety at a different site on the molecule, making the galactosylated product saccharide.

The term "sialic acid" or "sialic acid moiety" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The terms "CgtB from *C. jejuni*", "CgtB," or a nucleic acid encoding "CgtB from *C. jejuni*" or "CgtB" refer to nucleic acids and polypeptide polymorphic variants, alleles, mutants, interspecies homologs, and active truncated proteins disclosed herein, that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a CgtB nucleic acid from, e.g., *C. jejuni* strains OH4384 NCTC11168, and HS:10 (for exemplary CgtB nucleic acids, see, e.g., SEQ ID NOs:1, 3, 5, 7, or 9) or to an amino acid sequence of a CgtB from, e.g., *C. jejuni* strains OH4384 NCTC11168, and HS:10 (for exemplary CgtB protein sequences, see, e.g., SEQ ID NOs:2, 4, 6, 8, or 10); (2) bind to antibodies, e.g., polyclonal antibodies, raised against an immunogen comprising an amino acid sequence of a CgtB from *C. jejuni*, (examples above), and conservatively modified variants thereof; (3) specifically hybridize under stringent hybridization conditions to an anti-sense strand corresponding to a nucleic acid sequence encoding a CgtB from *C. jejuni*, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides, to a CgtB nucleic acid from *C. jejuni*, e.g., SEQ ID NOs:1, 3, 5, 7, or 9, or a nucleic acid encoding the catalytic domain. Preferably the catalytic domain has at least 90%, preferably at least 91%, 92%, 93%, 94%, 95%, 96%, 97%, 98%, 99% amino acid identity to the CgtB catalytic domain of SEQ ID NOs:2, 4, 6, 8, or 10. A polynucleotide or polypeptide sequence is typically from a bacteria including, but not limited to, *Campylobacter, Haemophilus*, and *Pasteurella*. The nucleic acids and proteins of the invention include both naturally occurring or recombinant molecules. A CgtB protein from *C. jejuni* typically has β-1,3-galactosyltransferase activity that can be assayed according to methods known to those of skill in the art, using appropriate donor substrates and acceptor substrates, as described herein. Some embodiments include truncated forms of the CgtB protein of, e.g., $CgtB_{11168}$ (Δ30), $CgtB_{HS:10}$ (Δ20) and $CgtB_{OH4384}$ ($_{Δ}$30). Additional embodiments include C-terminally truncated CgtB proteins fused to an MBP domain at the C-terminus of the protein, e.g., $CgtB_{11168}$ (Δ30, C-terminal MalE), $CgtB_{HS:10}$ (Δ20, C-terminal MalE) and $CgtB_{OH4384}$ (Δ30, C-terminal MalE).

"Commercial scale" refers to gram scale production of a galactosylated product in a single reaction. In preferred embodiments, commercial scale refers to production of greater than about 50, 75, 80, 90, 100, 125, 150, 175, or 200 grams of galactosylated product.

As used herein, a "truncated CgtB polypeptide" or grammatical variants, refers to a CgtB polypeptide that has been manipulated to remove at least one amino acid residue, relative to a wild-type CgtB polypeptide that occurs in nature, so long as the truncated CgtB polypeptide retains enzymatic activity. Examples of wild-type or naturally occurring CgtB proteins include, e.g., SEQ ID NOs:2, 4, 6, 8, or 10.

As used herein, a "maltose binding protein (MBP) domain" or grammatical variants, refers to an *E. coli* maltose binding domain protein. MBP domains are typically fused to proteins to enhance solubility of a the protein with a cell. See, e.g., Kapust and Waugh *Pro. Sci.* 8:1668-1674 (1999). Other maltose binding domains are known and can be fused to CgtB proteins as described herein, for example MBP domains from *Yersinia E. coli, Pyrococcus furiosus, Thermococcus litoralis, Thermatoga maritime*, and *Vibrio cholerae*. Amino acid linkers can be placed between the MBP domain and the CgtB protein.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed CgtB proteins. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, *Proteins* (1984)).

The cells and methods of the invention are useful for producing a galactosylated product, generally by transferring a galactose moiety from a donor substrate to an acceptor molecule. The cells and methods of the invention are also useful for producing a galactosylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys or a substantially identical variant thereof. Other suitable tags are known to those of skill in the art, and include, for example, an affinity tag such as a hexahistidine peptide, which will bind to metal ions such as nickel or cobalt ions or a myc tag. Proteins comprising purification tags can be purified using a binding partner that binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the art. Starch binding domains are described in WO 99/15636, herein incorporated by reference. Affinity purification of a fusion protein comprising a starch binding domain using a betacylodextrin (BCD)-derivatized resin is described in WO 2005/014779, published Feb. 17, 2005, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "fusion CgtB polypeptide" or a "fusion galactosyltransferase polypeptide" of the invention is a polypeptide that contains a CgtB or an β-1,3-galactosyltransferase catalytic domain. The fusion polypeptide is capable of catalyzing the synthesis of a sugar nucleotide (e.g., UDP-Galactose) as well as the transfer of the sugar residue from the sugar nucleotide to an acceptor molecule. Typically, the catalytic domains of the fusion polypeptides will be at least substantially identical to those of glycosyltransferases and fusion proteins from which the catalytic domains are derived. In some embodiments, a CgtB polypeptide and an epimerase, e.g., UDP-glucose 4' epimerase, polypeptide are fused to form a single polypeptide. For examples of a galactosyltransferase/UDP-glucose 4' epimerase see e.g. WO1999/031224, which is herein incorporated by reference for all purposes.

An "accessory enzyme," as referred to herein, is an enzyme that is involved in catalyzing a reaction that, for example, forms a substrate or other reactant for a glycosyltransferase reaction. An accessory enzyme can, for example, catalyze the formation of a nucleotide sugar that is used as a sugar donor moiety by a glycosyltransferase. An accessory enzyme can also be one that is used in the generation of a nucleotide triphosphate that is required for formation of a nucleotide sugar, or in the generation of the sugar which is incorporated into the nucleotide sugar. One example of an accessory enzyme is UDP-glucose 4' epimerase, e.g. GalE from *S. thermophilus* (accession umber M30175).

A "catalytic domain" refers to a portion of an enzyme that is sufficient to catalyze an enzymatic reaction that is normally carried out by the enzyme. For example, a catalytic domain of a CgtB polypeptide will include a sufficient portion of the CgtB to transfer a galactose moiety from a sugar donor to an acceptor saccharide. A catalytic domain can include an entire enzyme, a subsequence thereof; or can include additional amino acid sequences that are not attached to the enzyme or subsequence as found in nature.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a CgtB protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F (ab)'$_2$ may be reduced under mild conditions to break the disulfide linkage in the hinge region, thereby converting the F dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CgtB protein, polymorphic variants, alleles, orthologs, and conservatively modified variants, or splice variants, or portions thereof, can be selected to obtain only those polyclonal antibodies that are specifically immunoreactive with CgtB proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. CgtB Polypeptides

A CgtB polypeptide is a β-1,3-galactosyltransferase enzyme and has the functional activity of transferring galactose from UDP-galactose to an oligosaccharide comprising a terminal GalNAc residue on an oligosaccharide, disaccharide, or to a GalNAc monosaccharide. Examples of full-length, wild-type or naturally occurring CgtB proteins are, e.g., SEQ ID NO:2 or SEQ ID NO:4 or SEQ ID NO:6 or SEQ ID NO:8 or SEQ ID NO:10.

The truncated CgtB polypeptides of the invention comprise an amino acid sequence that is identical to or shares a specified percent identity with a portion of SEQ ID NO:2 or SEQ ID NO:4 or SEQ ID NO:6 or SEQ ID NO:8 or SEQ ID NO:10, i.e., SEQ ID NO:2, SEQ) ID NO:4, SEQ ID NO:6, SEQ ID NO:8, or SEQ ID NO:10 lacking between one and thirty amino acid residues from the C-terminus of the protein. In some embodiments, the truncated CgtB proteins also comprise an MBP domain fused to the C-terminus of the protein. The CgtB polypeptide is a β-1,3-galactosyltransferase enzyme and has the functional activity of transferring galactose from UDP-galactose to an oligosaccharide comprising a terminal N-acetyl-galactosamine.

Nucleic acids encoding proteins that are related to the CgtB protein from *C. jejuni* OH4384 were also identified in other *C. jejuni* strains, e.g., ATCC 43432, ATCC 43460 NCTC 11168 and ATC 43438. The amino acid sequences of these proteins are found at SEQ ID NO:4, SEQ ID NO:6, SEQ ID NO:8 and SEQ ID NO:10 respectively.

CgtB amino acid sequences can be analyzed to identify conserved amino acid residues. For example, the ClustalX program was used to align the $CgtB_{OH4384}$, $CgtB_{11168}$, and $CgtB_{HS10}$ proteins. Results are shown in FIG. 2. Identical amino acid residues in all three sequences are white on a black background; those identical between any two sequences are white on a gray background (see FIG. 2A). FIG. 2B shows the percentages of identity and similarity between any two of CgtB proteins as assigned in Genedoc.

Using the alignment generated by ClustalX or similar programs known to those of skill, identical, conserved, or semi-conserved residues can be identified and used to predict and avoid changes in amino acid residues that would be detrimental to CgtB activity. Such alignments can also be used to identify amino acid residues that can most likely be changed without affecting protein activity. Amino acid changes, if desired, can be made by selecting a conserved residue as identified herein or on the ClustalX website, or by selecting a modification to one of the corresponding amino acids in a figure such as FIG. 2.

IV. Isolation of Nucleic Acids Encoding CgtB Polypeptides

Nucleic acids that encode CgtB polypeptides include nucleic acids that encode the full-length, naturally occurring CgtB polypeptides described above, e.g., SEQ ID NO:2, SEQ ID NO:4, SEQ ID NO:6, SEQ ID NO:8 and SEQ ID NO:10 and enzymatically active truncations of those sequences. The CgtB polypeptides of the invention catalyze the transfer of a galactose moiety from a donor substrate to an acceptor substrate and assays to measure that activity are disclosed herein.

Nucleic acids that encode additional CgtB polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Standard molecular biology methods, e.g., PCR, can be used to generate truncations of any known CgtB sequence.

A DNA that encodes a CgtB polypeptide, or a subsequence thereof, can be prepared by any suitable method described above, including, for example, cloning and restriction of appropriate sequences with restriction enzymes. In one preferred embodiment, nucleic acids encoding CgtB polypeptides are isolated by routine cloning methods. A nucleotide sequence of a CgtB polypeptide as provided in, for example, SEQ ID NO:1, can be used to provide probes that specifically hybridize to a gene encoding a CgtB polypeptide in a genomic DNA sample; or to an mRNA, encoding a CgtB polypeptide comprising, in a total RNA sample (e.g., in a Southern or Northern blot). Once the target nucleic acid encoding a CgtB polypeptide is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length CgtB polypeptide, or subsequences thereof, e.g., containing subsequences encoding at least a subsequence of a catalytic domain of the CgtB polypeptide. These restriction enzyme fragments, encoding a CgtB polypeptide or subsequences thereof, may then be ligated, for example, to produce a nucleic acid encoding a CgtB protein.

A nucleic acid encoding a CgtB polypeptide, or a subsequence thereof, can be characterized by assaying for the expressed product. Assays based on the detection of the physical, chemical, or immunological properties of the expressed protein can be used. For example, one can identify a cloned CgtB nucleic acid, by the ability of a protein encoded by the nucleic acid to catalyze the transfer of a galactose moiety from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for CgtB activity, GalNAc-β-FCHASE can be used as a substrate. The reaction products of other glycosyltransferases can be detected using capillary electrophoresis, e.g., to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Wakarchuk, supra). To assay for α-2,8-sialyltransferase, GM3-FCHASE is used as a substrate. See, e.g., U.S. Pat. No. 6,503,744, which is herein incorporated by reference. Other methods for detection of oligosaccharide reaction products include thin layer chromatography and GC/MS and are disclosed in U.S. Pat. No. 6,503,744, which is herein incorporated by reference.

Also, a nucleic acid encoding a CgtB polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding CgtB polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired CgtB polypeptide or a subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the CgtB protein or a protein subsequence thereof by site-directed mutagenesis. The plasmid containing the CgtB protein-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) Science 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding bacterial CgtB proteins can be amplified using PCR primers based on the sequence of CgtB nucleic acids disclosed herein. Examples of PCR primers that can be used to amplify nucleic acid that encode CgtB proteins include the following primer pairs:

cgtB from *C. jejuni* OH4384 and related strains can be amplified using:

```
5'-end primer:
                                        (SEQ ID NO: 11)
CJ-133:   5' CTTAGGAGGTCATATGTTTAAAATTTCAATCATCTT
          ACC 3'

3'-end primer:
                                        (SEQ ID NO: 12)
CJ-105:   5' CCTAGGTCGACCTCTAAAAAAATATTCTTAACATT
          G 3'
``` cgtB from *C. jejuni* NCTC 11168 and related strains can be amplified using:

```
5'-end primer:
                                        (SEQ ID NO: 13)
CJ-179:   5' CTTAGGAGGTCATATGAGTCAAATTTCCATCATACTA
          CC 3'

3'-end primer:
                                        (SEQ ID NO: 14)
CJ-180   5' CCTAGGTCGACTTACGGAATTAAATTATATAAAATT
         TTTTCC 3'
``` cgtB from *C. jejuni* 0:10 and related strains can be amplified using:

```
5'-end primer:
                                        (SEQ ID NO: 15)
CJ-301    5' GCTGCTGGACATATGTTTAAAATTTCAATCATCTTGC
          C 3'

3'-end primer:
                                        (SEQ ID NO: 16)
CJ-300    5'CTTAGCGTCGACTTATTACATCTTCAGCAAGCGATAAA
          ATTTAAATTG 3'
```

In some bacteria, nucleic acids encoding CgtB protein can be isolated by amplifying a specific chromosomal locus, e.g., the LOS locus of *C. jejuni*, and then identifying a CgtB nucleic acid typically found at that locus (see, e.g., U.S. Pat. No. 6,503,744). Examples of PCR primers that can be used to amplify an LOS locus comprising nucleic acids encoding a CgtB protein include the following primer pairs:

```
CJ42: Primer in heptosylTase-II
5' GC CAT TAC CGT ATC GCC TAA CCA GG 3' 25 mer CJ43: Primer in heptosylTase-I
5' AAA GAA TAC GAA TTT GCT AAA GAG G 3' 25 mer
```

Other physical properties of a recombinant CgtB polypeptide expressed from a particular nucleic acid, can be compared to properties of known CgtB polypeptides to provide another method of identifying suitable sequences or domains of the CgtB polypeptide that are determinants of acceptor substrate specificity and/or catalytic activity. Alternatively, a putative CgtB polypeptide or recombinant CgtB polypeptide can be mutated, and its role as a glycosyltransferase, or the role of particular sequences or domains established by detecting a variation in the structure of a carbohydrate normally produced by the non-mutated, naturally-occurring, or control CgtB polypeptide. Those of skill will recognize that mutation or modification of CgtB polypeptides of the invention can be facilitated by molecular biology techniques to manipulate the nucleic acids encoding the CgtB polypeptides, e.g., PCR.

Functional domains of newly identified CgtB polypeptides can be identified by using standard methods for mutating or modifying the polypeptides and testing them for activities such as acceptor substrate activity and/or catalytic activity, as described herein. The functional domains of the various CgtB polypeptides can be used to construct nucleic acids encoding CgtB polypeptides and the functional domains of one or more CgtB polypeptides. These multi-CgtB fusion proteins can then be tested for the desired acceptor substrate or catalytic activity.

In an exemplary approach to cloning nucleic acids encoding CgtB proteins, the known nucleic acid or amino acid sequences of cloned CgtB polypeptides are aligned and compared to determine the amount of sequence identity between various CgtB polypeptides. This information can be used to identify and select protein domains that confer or modulate CgtB activities, e.g., acceptor substrate activity and/or catalytic activity based on the amount of sequence identity between the CgtB proteins of interest. For example, domains having sequence identity between the CgtB proteins of interest, and that are associated with a known activity, can be used to construct CgtB proteins containing that domain, and having the activity associated with that domain (e.g., acceptor substrate specificity and/or catalytic activity).

V. Expressing cgtB Polypeptides in Host Cells

CgtB proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella.*

Once expressed in a host cell, the CgtB polypeptides can be used to produced galactosylated products. For example, the CgtB polypeptides can be isolated using standard protein purification techniques and used in in vitro reactions described herein to make galactosylated products. Partially purified CgtB polypeptides can also be used in vitro reactions to make galactosylated products as can the permeabilized host cells. The host cells can also be used in an in vivo system (e.g., fermentative production) to produce galactosylated products.

Typically, the polynucleotide that encodes the CgtB polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res*. (1980) δ: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of CgtB proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the CgtB proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi Aspergillus (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol*.; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promote is described in PCT Patent Application Publ. No. WO98/20111.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The CgtB polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the CgtB polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the CgtB proteins are fused to a subsequence of protein A or bovine serum albumin (BSA), for example, to facilitate purification, secretion, or stability.

The CgtB polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

VI. Purification of CgtB Polypeptides

The CgtB proteins of the present invention can be expressed, e.g., as intracellular proteins or as proteins that are secreted from the cell, and can be used in this form, in the methods of the present invention. For example, a crude cellular extract containing the expressed intracellular or secreted CgtB polypeptide can used in the methods of the present invention.

Alternatively, the CgtB polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the CgtB polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the CgtB polypeptide of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilotri-acetic acid (NTA) (Hochuli, E. (1990) "Purification of recombinant proteins with metal chelating adsorbents" In Genetic Engineering Principles and Methods, J. K. Setlow, Ed., Plenum Press, NY; commercially available from Qiagen (Santa Clarita, Calif.)). Other purification or epitope tags include, e.g., AU1, AU5, DDDDK (EC5), E tag, E2 tag, Glu-Glu, a 6 residue peptide, EYMPME, derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a CgtB polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the CgtB polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VII. Donor Substrates and Acceptor Substrates

Suitable donor substrates used by the CgtB polypeptides include e.g., UDP-Gal. Guo et al., *Applied Biochem. and Biotech.* 68: 1-20 (1997).

Typically, acceptor substrates include a terminal GalNAc residue or derivatives for addition of a galactose residue by an β-1,3 linkage. Examples of suitable acceptors include a terminal GalNAc that is linked to Gal by a β1,4 linkage, and a terminal GalNAc that is linked directly to an aglycone group at the reducing end. Suitable labeled acceptors, include, for example, GalNAcβ-1,4-Galβ-1,4-Glc-FCHASE, GalNAcβ-1,4-[NeuAcα-2,3]-Galβ-1,4-Glc-FCHASE, GalNAcβ-1,4-[NeuAc-α-2,3]-Galβ-1,4-Glc-sphingosine-FCHASE, GalNAcβ-1,4-[NeuAcα-2,8-NeuAcα-2,3]-Galβ-1,4-Glc-FCHASE, GalNAcβ-FCHASE, GalNAc-α-FCHASE, GalNAc-β-p-Nitrophenyl, GalNAc-α-p-Nitrophenyl. In some embodiments, the acceptor residue is a portion of an oligosaccharide that is attached to a peptide, a protein, a lipid, or a proteoglycan, for example. FCHASE-NH-Val-Gly-Val-Thr[GalNAc-α-]Glu-Thr-Pro-COOH, IFNα2b[Thr-134-GalNAc. Truncated CgtB proteins can also be used to add galactose residues to unlabeled acceptor substrates with, e.g., the structures listed above. Unlabeled acceptor substrates are used, e.g., to make galactosylated products on a commercial scale.

Suitable acceptor substrates used by the CgtB polypeptides and methods of the invention include, but are not limited to, polysaccharides and oligosaccharides. The CgtB polypeptides described herein can also be used in multienzyme systems to produce a desired product from a convenient starting material.

Suitable acceptor substrates used by the CgtB polypeptides and methods of the invention include, but are not limited to, proteins, lipids, peptides, glycoproteins, glycolipids, glycopeptides, gangliosides and other biological structures (e.g., whole cells) that can be modified by the methods of the invention. These acceptor substrates will typically comprise the polysaccharide or oligosaccharide molecules described above. Exemplary structures, which can be modified by the methods of the invention include any a of a number glycolipids, glycoproteins and carbohydrate structures on cells known to those skilled in the art.

The present invention provides CgtB polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide.

For synthesis of glycoproteins, one can readily identify suitable CgtB polypeptides by reacting various amounts of a CgtB polypeptide of interest (e.g., 0.01-100 mU/mg protein) with a glycoprotein (e.g., at 1-10 mg/ml) to which is linked an oligosaccharide that has a potential acceptor site for glycosylation by the CgtB protein of interest. The abilities of the recombinant CgtB proteins of the present invention to add a sugar residue at the desired acceptor site are compared, and a CgtB polypeptide having the desired property (e.g., acceptor substrate specificity or catalytic activity) is selected.

In general, the efficacy of the enzymatic synthesis of oligosaccharides, glycoproteins, and glycolipids, having desired galactosylated oligosaccharide moieties, can be enhanced through use of recombinantly produced CgtB polypeptides of the present invention. Recombinant techniques enable production of the recombinant CgtB polypeptides in the large amounts that are required for large-scale in vitro oligosaccharide, glycoprotein and glycolipid modification.

In some embodiments, suitable oligosaccharides, glycoproteins, and glycolipids for use by the CgtB polypeptides and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

VIII. Production of Galactosylated Products

CgtB polypeptides can be used to make galactosylated products in vitro reactions mixes or by in vivo reactions, e.g., by fermentative growth of recombinant microorganisms that comprise nucleotides that encode CgtB polypeptides.

A. In vitro Reactions

The CgtB polypeptides can be used to make galactosylated products in vitro reactions mixes. The in vitro reaction mixtures can include permeabilized microorganisms comprising the CgtB polypeptides, partially purified CgtB polypeptides, or purified CgtB polypeptides; as well as donor substrates acceptor substrates, and appropriate reaction buffers. For in vitro reactions, the recombinant glycosyltransferase proteins, such as CgtB polypeptides, acceptor substrates, donor substrates and other reaction mixture ingredients are combined by admixture in an aqueous reaction medium. Additional glycosyltransferases can be used in combination with the CgtB polypeptides, depending on the desired galactosylated product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular galactosyltransferase used. For CgtB polypeptides, the pH range is preferably maintained from about 7.0 to 8.0. For sialyltransferases, the range is preferably from about 5.5 to about 8.0.

Enzyme amounts or concentrations are expressed in activity units, which is a measure of the initial rate of catalysis. One activity unit catalyzes the formation of 1 µmol of product per minute at a given temperature (typically 37° C.) and pH value (typically 7.5). Thus, 10 units of an enzyme is a catalytic amount of that enzyme where 10 µmol of substrate are converted to 10 µmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the biomolecule to be glycosylated. For large-scale preparations, the reaction will often be allowed to proceed for between about 0.5-240 hours, and more typically between about 1-36 hours.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al., *J. Am. Chem. Soc.* 117:5869-5870 (1995), and Ichikawa et al. *In Carbohydrates and Carbohydrate Polymers*. Yaltami, ed. (ATL Press, 1993).

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

B. In vivo Reactions

The CgtB polypeptides can be used to make galactosylated products by in vivo reactions, e.g., fermentative growth of recombinant microorganisms comprising the CgtB polypeptides. Fermentative growth of recombinant microorganisms can occur in the presence of medium that includes an acceptor substrate, e.g. GalNAc and a donor substrate or a precursor to a donor substrate, e.g., galactose. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of galactosylated products is enhanced by manipulation of the host microorganism. For example, in *E. coli*, break down of sialic acid can be minimized by using a host strain that is lacking, e.g., CMP-sialate synthase (NanA-). (In some strains of *E. coli*, CMP-sialate synthase appears to be a catabolic enzyme.) Also in *E. coli*, when lactose is, for example, the acceptor saccharide or an intermediate in synthesizing the galactosylated product, lactose breakdown can be minimized by using host cells that are LacZ-.

C. Characterization of and Isolation of Galactosylated Products

The production of galactosylated products can be monitored by e.g., determining that production of the desired product has occurred or by determining that a substrate such as the acceptor substrate has been depleted. Those of skill will recognize that galactosylated products such as oligosaccharide, can be identified using techniques such as chromatography, e.g., using paper or TLC plates, or by mass spectrometry, e.g., MALDI-TOF spectrometry, or by NMR spectroscopy. Methods of identification of galactosylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

The products produced using CgtB polypeptides can be used without purification. However, standard, well known techniques, for example, thin or thick layer chromatography, ion exchange chromatography, or membrane filtration can be used for recovery of galactosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through. Glycoprotein galactosylated products can be isolated or purified using standard protein purification techniques, including those described herein.

EXAMPLES

Lipooligosaccharide (LOS) structures found in *C. jejuni* strains are structurally diverse, and the diversity correlates with the glycosyltransferases expressed from the LOS locus. For example, galactose is added in a β-1,3 configuration by the CgtB protein. The structure of the galactosylated oligosaccharide product varies in different *C. jejuni* strains as does the sequence of the CgtB protein, see, e.g., FIGS. 1 and 2. However, various naturally-occurring CgtB proteins all have β-1,3-galactosyltransferase activity. The present study identifies core CgtB structures required for β-1,3-galactosyltransferase activity and surprisingly improved enzymatic activities associated with modified CgtB proteins.

Abbreviations used in the following examples are as follows: CE, capillary electrophoresis; FCHASE, 6-(fluorescein-5-carbaxamido)hexanoic acid, succinimidyl ester; HEPES, N-(2-hydroxyethyl)piperazine-N'-2-ethanesulfonic acid; IPTG, isopropyl-1-thio-β-D-galactopyranoside, LOS, lipooligosaccharide; LPS, lipopolysaccharide; MES, 2-(N-Morpholino)ethanesulfonic acid; PCR, polymerase chain reaction.

The acceptor sugars used in CgtB enzyme assays throughout his report were named after their corresponding gangliosides headgroups (even if they only consist in their glycone moiety, except in the case of lyso-GM2). Hence, GA2 is GalNAcβ-1,4-Galβ-1,4-Glc-FCHASE, GM2-FCHASE is GalNAcβ-1,4-[NeuAcα-2,3]-Galβ-1,4-Glc-FCHASE, lyso-GM2 is GalNAcβ-1,4-[NeuAc-α-2,3]-Galβ-1,4-Glc-sphingosine-FCHASE. GD3-FCHASE is NeuAcα-2,8-NeuAcα-2,3-Galβ-1,4-Glc-FCHASE and GM3-FCHASE is NeuAcα-2,3-Galβ-1,4-Glc-FCHASE. The product of the CgtB reaction, GM1a-FCHASE, is Galβ-1,3-GalNAcβ-1,4-[NeuAcα-2,3]-Galβ-1,4-Glc-FCHASE. IFNα2b[Tn]-FCHASE is IFNα2b[GalNAcα]-FCHASE, IFNα2b[T-Ag]-FCHASE is IFNα2b[Galβ1,3-GalNAcα]-FCHASE (the labeled peptide acceptor in both instances); IFNα2b[Tn] is IFNα2b[GalNAcα], IFNα2b[T-Ag] is IFNα2b[Galβ1,3-GalNAcα] (the protein acceptor in both instances).

Example 1

CgtB Variants Sequence Comparison and Analysis

Three classes of naturally occurring CgtB proteins have been identified and are represented by CgtB proteins from three *C. jejuni* strains: CgtB$_{OH4384}$, CgtB$_{11168}$, and CgtB$_{OH:10}$. A multiple sequence alignment of the naturally occurring CgtB proteins is shown in FIG. 2A. Pairwise comparisons using any two of the three CgtB proteins show that they share 54-59% sequence identity and 67-75% sequence similarity over the full-length sequence (FIG. 2B). The highly-conserved amino-terminal domain of CgtB is thought to be the donor-binding domain. In CgtB, this domain has been delineated as the first 108 positions based on sequence identity between the three sequences. Pair-wise comparisons of the N-terminal domain between any two CgtB proteins show that the N-terminal domain is highly conserved, with any two CgtB proteins sharing at least 87% sequence identity and at least 92% sequence similarity (FIG. 2B).

The carboxy-terminal domain of the CgtB protein is the acceptor-binding domain and comprises positions 109 to the end of CgtB. Pair-wise comparisons using the C-terminal domains reveal more sequence divergence, with any two CgtB proteins sharing at least 37% sequence identity and at least 54% sequence similarity (FIG. 2B). The sequence divergence observed in the acceptor-binding domains correlates with the observed differences in acceptor LOS molecules, e.g., with or without branched sialic acid residues in their outer core.

Nucleic acids to express truncated CgtB proteins were constructed to determine minimum amino acid structures required for activity of $CgtB_{OH4384}$, $CgtB_{11168}$, and $CgtB_{OH:10}$.

Example 2

Constructs and Protein Purification

The bacterial strains and plasmids used in this work are listed in Table I.

TABLE I

Bacterial strains, plasmids and oligonucleotides used in this work

| Strain/plasmid name *E. coli* | Genotype/Relevant information | Reference |
|---|---|---|
| AD202 | $F^-$ ΔaraD139 DE(argF-lac)169 ompT1000::kan $LAM^-$ flhD5301 fruA25 relA1 rpsL150($str^R$) rbsR22 deoC1 | Akiyama and Ito, 1990 |
| CJL-10 | AD202 + pCJL10 | This work |
| CJL-20 | AD202 + pCJL20 | This work |
| CJL-29 | AD202 + pCJL29 | This work |
| CJL-94 | AD202 + pCJL94 | This work |
| CJL-115 | AD202 + pCJL115 | This work |
| CJL-122 | AD202 + pCJL122 | This work |
| CJL-136 | AD202 + pCJL136 | This work |
| CJL-137 | AD202 + pCJL137 | This work |
| CJL-177 | AD202 + pCJL177 | This work |
| Plasmids | | |
| pCWori+ | Expression vector used in this work | Wakarchuk et al. 1994 |
| pCWmalE-N | pCWori+ containing malE to engineer N-terminal protein fusions | This work |
| pCWmalE-C | pCWori+ containing malE to engineer C-terminal protein fusions | This work |
| pCJL10 | pCWmalE-N/NdeI-SalI + $cgtB_{OH4384}$/NdeI-SalI | This work |
| pCJL20 | pCWmalE-N/NdeI-SalI + $cgtB_{11168}$/NdeI-SalI | This work |
| pCJL29 | pCWmalE-N/NdeI-SalI + $cgtB_{HS:10}$/NdeI-SalI | This work |
| pCJL94 | pCWmalE-N/NdeI-SalI + $cgtB_{11168}$-90 bp/NdeI-SalI | This work |
| pCJL115 | pCWmalE-N/NdeI-SalI + $cgtB_{HS:10}$-60 bp/NdeI-SalI | This work |
| pCJL122 | pCWmalE-N/NdeI-SalI + $cgtB_{OH4384}$-90 bp/NdeI-SalI | This work |
| pCJL136 | pCWmalE-C/NdeI-EcoRI + $cgtB_{OH4384}$-90 bp/NdeI-EcoRI | This work |
| pCJL137 | pCWmalE-C/NdeI-EcoRI + $cgtB_{11168}$-90 bp/NdeI-EcoRI | This work |
| pCJL177 | pCWmalE-C/NdeI-EcoRI + $cgtB_{HS:10}$-60 bp/NdeI-EcoRI | This work |

*E. coli* strains were maintained on 2YT (BIO 101, Carlsbad, CA) plates. For growth of *E. coli* in liquid medium (2YT), cultures were inoculated from fresh overnight cultures, grown at 37° C. for 2 hours, supplemented with IPTG to a final concentration of 1 mM and were grown at 20° C. for an additional 24 hours before harvest. When required, ampicillin was added to 150 μg/mL.

All the oligonucleotide primers used for this work are listed in FIG. 5A-C. Amplification reactions were done using purified *C. jejuni* DNA as described previously (Gilbert, M. et al., *J Biol. Chem.* 277:327-337 (2002)). Amplicons were purified using the QIAquick PCR Purification Kit (QIAGEN Inc., Mississauga, Ontario) and cloned as fragments with either NdeI and SalI ends (in pCWori+ or pCWmalE-N) or with EcoRI and SalI termini (in pCWmalE-C). pCWmalE-C and pCWmalE-N were used to make C-terminal and N-terminal MalE fusion proteins (malE codes for maltose binding protein). DNA sequencing reactions were performed as described previously (Gilbert, M. et al., *J Biol. Chem.* 277: 327-337 (2002)). The nucleotide sequences of cgtB from various serotypes of *C. jejuni* are available in Genbank (entries AF130984, AF400048 and AL139077 for $cgtB_{OH4384}$, $cgtB_{HS:10}$ and $cgtB_{11168}$, respectively). Similarity and identity percentages between CgtB sequences were determined using Pairwise BLAST (BLAST 2 Sequences; online at ncbi.nlm.nih.gov/blast/bl2seq/bl2.html).

Cells grown in liquid cultures as described above were resuspended at 10% (w/v) in NaHEPES 20 mM pH 7.0, 200 mM NaCl, 5 mM β-mercaptoethanol, 1 mM EDTA, 10% glycerol (Buffer A) and were lysed by two passages through an Emulsiflex (Avestin, Ottawa, Ontario). The cell lysate was centrifuged at 20 000×g for 30 minutes at 4° C. (SS-34 rotor). The supernatant was diluted as needed in buffer A and applied to a 20 mL column of amylose resin (New England Biolabs, Ltd., Pickering, Ontario). After sample application, the column was washed with 2 column volumes to elute unbound proteins. The bound protein was eluted by washing the column with buffer B (Buffer A with 20 mM maltose) and the eluate was collected in 2 mL fractions. The fractions containing the eluted protein were pooled and dialysed overnight against 100 volumes of sodium acetate 50 mM pH6.0, glycerol 20% at 4° C. Protein quantitation was done using the BCA reagent (Pierce).

Example 3

Enzyme Assays

The oligosaccharide acceptors and the interferon alpha 2b (IFNα2b) peptide (VGVTETP, corresponding to positions 103-109 of the mature IFNα2b protein) were labeled with FCHASE as previously described (Wakarchuk, W. et al., *J Biol. Chem.* 271:19166-19173 (1996)). IFNα2b-FCHASE was purified by reverse-phase chromatography using a PRP-1 column (10×250 mm, Hamilton Company, Reno, Nev.) in 10 mM ammonium acetate pH 5.5 with a gradient of acetonitrile (0-100% over 4 column volumes). CgtB activity assays were done in cell lysates or using purified enzyme in 50 mM MES pH 6.0, 0.5 mM of FCHASE-acceptor (unless otherwise indicated), 10 mM MnCl$_2$, 10 mM DTT, 1 mM UDP-Gal at 37° C. from 5 to 30 minutes. All reactions were stopped by addition of 10 μL of 50% acetonitrile, 10 mM EDTA and 1% SDS and were diluted with H$_2$O to obtain 10-15 μM final concentration of the FCHASE-labeled compounds. The samples were analyzed by capillary electrophoresis as described previously (Wakarchuk, W. W. et al., *Methods Mol. Biol.* 213:263-274 (2003)) except that a P/ACE MDQ Capillary Electrophoresis System equipped with a Laser module 488 (Beckman Coulter, Calif.) was used. Quantitation of the reactions was performed by integration of the trace peaks using the MDQ 32 Karat software.

Example 4

Glycosylation of IFNα2b-FCHASE and IFNα2b

The IFNα2b protein was purchased from Cell Sciences (Canton, Mass.). IFNα2b-FCHASE and IFNα2b were converted into IFNα2b[Tn]-FCHASE and IFNα2b[Tn] using GALNT2-MBP (a gift from NEOSE Technologies) (DeFrees, S. et al. *Glycobiology.* 16:833-843 (2006)). IFNα2b [Tn]-FCHASE was purified by reverse-phase chromatography as described above. IFNα2b[Tn] was purified by cation-exchange chromatography using a Mini S 4.6/5.0 column (GE Healthcare Bio-Sciences, Baie d'Urfé, Québec) using a 0.01-1 M gradient of NH$_4$OAc pH 4.5.

Purified IFNα2b[Tn]-FCHASE 500 μg (360 nanomoles) was converted into IFNα2b[T-Ag]-FCHASE in a reaction containing 15 mU of purified CJL-136, 50 mM MES pH 6.0, 10 mM MnCl$_2$, 1 mM DTT and 2 mM UDP-Gal. The reaction was stopped after 30 minutes, cleaned on a Sep Pak C18 column (Waters Corporation, Milford, Mass.) and the IFNα2b[T-Ag]-FCHASE was purified by reverse-phase chromatography as described above.

IFNα2b[Tn] was converted in to IFNα2b[T-Ag] in 1 mL reactions containing 2.5 mg of IFNα2b[Tn], 10 mM MnCl$_2$, 1 mM DTT, 2 mM UDP-Gal, 50 mM NaCl, in 50 mM NaOAc pH 6.0 and 5 mU of purified CJL-136.

The reaction was left overnight at room temperature. The next day, the reaction was supplemented with 1 mM UDP-Gal and 2.5 mU of purified CJL-136. The newly synthesized IFNα2b[T-Ag] was purified by cation-exchange chromatography as described above.

Example 5

Mass Spectrometry

A Prince CE system (Prince Technologies, Emmen, The Netherlands) was coupled to a 4000 QTRAP mass spectrometer (Applied Biosystems/MDS Sciex, Streetsville, Canada). A sheath solution (isopropanol-methanol, 2:1) was delivered at a flow rate of 1.0 μL/min. Separations were obtained on about 90 cm length bare fused-silica capillary using 15 mM ammonium acetate in deionized water, pH 9.0. The 5 kV of electrospray ionization voltage were used for positive ion mode. MALDI-TOF mass spectra were acquired on a Voyager-DE STR mass spectrometer (Applied Biosystems, Foster City, Calif.) equipped with a pulsed nitrogen laser (337 nm), with a voltage of 20 kV as the accelerating voltage in the positive mode.

Example 6

Acceptor Preferences of CgtB Variants

Each full length CgtB protein was expressed as an N-terminal fusion with the MalE protein from *E. coli* (Table I) and was purified. The three purified enzymes were then assayed with the synthetic acceptors GalNAcα-, GalNAcβ-, GM2[1]-, lyso-GM2[1]- and GA2[1]-FCHASE to investigate their acceptor preference (Table II). This data represents a screening of the activity of each CgtB variant on various acceptors. The data of Table II is presented in relative activity, in which the activity measured on GM2-FCHASE was used as the reference for CM-10 (CgtB$_{OH4384}$ (FL, N-terminal MalE)) and CJL-20 (CgtB$_{11168}$ (FL, N-terminal MalE)) while the activity on GA2-FCHASE was the reference for CJL-29 (CgtB$_{OH:10}$ (FL, N-terminal MalE)). The reference acceptor for each CgtB protein was chosen on the basis of its structural similarity with the structure of the LOS of the corresponding strain (FIG. 1).

The activity trends indicated that CgtB$_{OH4384}$ (FL, N-terminal MalE) and CgtB$_{11168}$ (FL, N-terminal MalE) were most active with the lyso-GM2-FCHASE acceptor, compared to the non-lipid containing acceptor GM2-FCHASE. The activity with either monosaccharide acceptor was also lower than that of the tetra-saccharide GM2-FCHASE (Table II). In the case of CgtB$_{OH:10}$ (FL, N-terminal MalE), its activity with the non-sialylated acceptor GA2-FCHASE was significantly higher than that with any sialylated acceptor or monosaccharide acceptor (Table II).

TABLE II

Initial substrate survey of the acceptor preference of N-terminal MalE-CgtB fusions

| Acceptor[1] | Relative activity (%)[2] | | |
|---|---|---|---|
| (FCHASE-labeled, used at 0.5 mM) | CgtB$_{OH4384}$ (FL, N-terminal MalE) | CgtB$_{11168}$ (FL, N-terminal MalE) | CgtB$_{OH:10}$ (FL, N-terminal MalE) |
| GalNAcα- | 6.4[3] | 3.0[3] | 1.4[3] |
| GalNAcβ- | 47.5[4] | 50.5[4] | 1.9[4] |
| GM2- | 100[4] | 100[4] | 3.8[4] |
| lysoGM2- | 444[4] | 606.2[4] | 0.3[4] |
| GA2- | 29[3] | 8.8[3] | 100[3] |

[1]See the list of abbreviations.
[2]GM2-FCHASE was chosen as the reference acceptor for CgtB$_{OH4384}$ and CgtB$_{11168}$ while GA2-FCHASE was chosen as the reference acceptor for CgtB$_{HS:10}$.
[3]average of two experiments
[4]average of three experiments Taken together, these data indicate that the three CgtB proteins have different acceptor preferences. In particular, the differences observed between sialylated and non-sialylated acceptors (GM2-, lyso-GM2- vs. GA2-FCHASE) show that the sialylation of the acceptor is an important determinant in acceptor preference. This perfectly correlates with the sialylation state of the inner core LOS of each strain in vivo. The higher activity of CgtB$_{OH4384}$ (FL, N-terminal MalE) and CgtB$_{11168}$ (FL, N-terminal MalE) with lyso-GM2-FCHASE is attributable to the sphingosine lipid aglycone of the acceptor which mimics the lipid A portion of the natural LOS acceptor.

Example 7

CgtB Enzyme Improvement: Construction of Carboxy-Terminal Deletions

The expression of unmodified cgtB in *E. coli* did not lead to visible over-production of CgtB protein. The protein was completely associated with the membrane (Gilbert, M et al., *J Biol. Chem.* 275:3896-3906 (2000); Linton, D. et al., *Mol. Microbiol.* 37:501-14 (2000)). It has been shown with other bacterial glycosyltransferases that removal of short stretches of C-terminal residues can lead to an increase in solubility for the recombinant enzymes in *E. coli* (Wakarchuk, W. W. et al., *Protein Eng.* 11:295-302 (1998); Chiu, C. P. et al., *Nat Struct Mol Biol.* 11:163-170 (2004)). Ten, twenty, and thirty amino acids were truncated from the C terminus of $CgtB_{OH4384}$ and $CgtB_{11168}$ proteins, but these modified proteins were not any more soluble nor were they expressed at a much higher level than the parent construct (data not shown). The truncations were next incorporated into the N-terminal MalE-CgtB fusion proteins, as these fusion proteins were somewhat soluble to begin with. The truncations did not much improve the solubility of these fusion proteins, and in fact the longer deletions were deleterious to the activity (Table III).

TABLE III

Specific activity of purified CgtB proteins using FCHASE-labeled acceptors

| Enzyme | Specific Activity (mU/mg) on a given FCHASE-labeled acceptor | | | | |
|---|---|---|---|---|---|
| | 3 mM GalNAcα- | 3 mM GalNAcβ- | 1 mM GM2- | 1 mM GA2- | 1 mM IFNα2b[Tn]- |
| CJL-10 $CgtB_{OH4384}$ FL, N-terminal MalE | 158[1] | 192 | 210 | ND | 83.5 |
| CJL-122 $CgtB_{OH4384}$ Δ30, N-terminal MalE | 49.5 | 36 | 96 | ND | 14 |
| CJL-136 $CgtB_{OH4384}$ Δ30, C-terminal MalE | 531.5 | 1299.5 | 2420 | ND | 271.5 |
| CJL-20 $CgtB_{11168}$ FL, N-terminal MalE | 13.6 | 40.4 | 27 | ND | ND[2] |
| CJL-94 $CgtB_{11168}$ Δ30, N-terminal MalE | 0.9 | 5.3 | 14 | ND | ND |
| CJL-137 $CgtB_{11168}$ Δ30, C-terminal MalE | 11.6 | 75.7 | 80.9 | ND | ND |
| CJL-29 $CgtB_{OH:10}$ FL, N-terminal MalE | 9.7 | 4.8 | 4.5 | 86.9 | ND |
| CJL-115 $CgtB_{OH:10}$ Δ20, N-terminal MalE | 3.3 | 8.0 | 2.3 | 34.4 | ND |
| CJL-177 $CgtB_{OH:10}$ Δ20, N-terminal MalE | 58.1 | 127.5 | 17.5 | 374.0 | ND |

[1]CJL-10, CJL-122 and CJL-136 may add more than 1 galactosyl residue to their acceptor.
[2]For the CgtB enzyme from the 11168 only very low-level conversion was detectable on the glycopeptide acceptor by capillary electrophoresis <5%.

The C-terminal truncation of 10 and 20 amino acid residues from both $CgtB_{OH4384}$ and $CgtB_{11168}$ proteins did not purify well in preliminary purifications and were not pursued further. The 30 amino acid residue deletions were deleterious to the activity of both $CgtB_{OH4384}$ and $CgtB_{11168}$ proteins, but these proteins could be purified and characterized, perhaps because they are slightly more soluble. The full length CgtB proteins fused to MalE at the N-terminus showed better activity with all the acceptors tested as compared to the corresponding truncated CgtB proteins fused to MalE at the N-terminus, and this ranged from about 2 to as much as 15 fold in activity (Table III)

With $CgtB_{OH:10}$, only the 20 amino acid truncation was studied as the other two truncations were not very active. In this case, the decrease in activity after truncation is seen only on the α-anomer of GalNAc but the activity on the beta-anomer actually increases slightly. The activity on the "best" acceptor GA2-FCHASE also decreased after truncation of the protein as was observed with the other enzyme/acceptor combinations.

Example 8

Inversion of the Fusion Order and Impact on CgtB Specific Activity

The data from the previous example showed that the carboxy-terminal end of CgtB was important for acceptor interactions and sensitive to truncation. Inversion of the fusion was assessed by fusing MalE to the C-terminus of truncated CgtB proteins. These fusions were constructed, purified and assayed as previously described. Once these truncated CgtB-MalE C-terminal fusions had been generated, they were used in side-by-side comparisons with the other CgtB constructs to evaluate which proteins were the most active, and toward which acceptor (Table III). Surprisingly, the reversed gene order, i.e., C-terminal MalE fusions rather than N-terminal MalE fusions, produced CgtB proteins that are far more active than the previously constructed CgtB fusions and truncations. As an example, using the tetrasaccharide GM2-FCHASE as an acceptor, the $CgtB_{OH4384}$ (Δ30, C-terminal MalE) protein shows as much as a 11-fold increase over the $CgtB_{OH4384}$ (FL, N-terminal MalE) protein. This improvement was also significant in that a glycopeptide acceptor, which is a model system for producing the core 1 O-glycosylation on a human protein (see below), could now be effectively modified.

Although not as pronounced, the surprising trend of improved activity from the CgtB-C-terminal-MalE fusions was also seen with CgtB from *C. jejuni* strains NCTC11168 and OH:10 (Table III). Some differences were seen; one notable exception is that of $CgtB_{11168}$ (Δ30, C-terminal MalE) on the α-anomer of GalNAc where the activity is unchanged.

$CgtB_{OH4384}$ (Δ30, C-terminal MalE) had the highest specific activities among all CgtB proteins tested (Table III). Therefore, its kinetic parameters were investigated using the monosaccharide acceptors GalNAcα-FCHASE and GalNAcβ-FCHASE and for its donor sugar UDP-Gal (Table IV).

TABLE IV

Kinetic parameters of enzyme from $CgtB_{OH4384}$ (Δ30, C-terminal MalE)

| Substrate | $K_{m(app)}$ (mM) | $V_{max}$ (mU/mg prot.)[1] | $k_{cat\,(app)}$ (min$^{-1}$) | $k_{cat}/K_m$ (min$^{-1}$ × mM$^{-1}$) |
|---|---|---|---|---|
| GalNAcα-FCHASE | 1.68 ± 0.19 | 413 ± 18.3 | 30.2 | 18.0 |
| GalNAcβ-FCHASE | 3.18 ± 1.02 | 878 ± 142 | 64.1 | 20.2 |
| UDP-Gal[2] | 1.11 ± 0.1 | 47 ± 1.5 | 3.4 | 3.1 |

[1]one unit of activity is defined as the conversion of 1 μmol of the substrate tested in 1 minute.
[2]determined using 5 mM GalNAcβ-FCHASE which is the limit of solubility for this acceptor, which means these kinetic parameters are estimates only Attempts to obtain kinetic parameters with N-terminal MalE-CgtB had been hampered by the low solubility of the monosaccharide acceptors, meaning that conditions of acceptor saturation could never be approached (data not shown). Because of the solubility limitations of the two monosaccharide acceptors, the assays were not performed under saturating conditions; the values reported in Table IV are therefore estimates of the actual kinetic parameter. The $K_{m(app)}$ value for GalNAcα-FCHASE is 1.68 mM and that for GalNAcβ-FCHASE is 3.18 mM. The $K_{m(app)}$, $V_{max}$ and $k_{cat}$ values for GalNAcβ-FCHASE are 2.1 times higher than those for Gal-NAcα-FCHASE. However, the specificity constant, $k_{cat}/K_m$, is very similar for the two acceptors which indicates that CgtB$_{OH4384}$ (Δ30, C-terminal MalE) does not discriminate strongly between these 2 anomers, which makes this enzyme a very good catalyst for producing the core 1 type disaccharide.

Example 9

Activity on the IFNα2b[Tn]-FCHASE Peptide

The highest activity measured for GalNAcα-FCHASE was that of CgtB$_{OH4384}$ (Δ30, C-terminal MalE) (531.5 mU/mg, Table III). Thus, CgtB$_{OH4384}$ (Δ30, C-terminal MalE) was evaluated as a tool to elaborate O-linked glycans on peptides and proteins. The N-terminal MalE CgtB$_{OH4384}$ constructs (full length and Δ30) were also tested for comparison. The analysis of the galactosylation of IFNα2b[Tn]-FCHASE after 30 minutes by capillary electrophoresis showed that 91.9% of the material had been converted into IFNα2b[T-Ag]-FCHASE and there was also 4.4% of unwanted side-products (4.3% and 0.1% of IFNα2b[Gal-T-Ag]-FCHASE and IFNα2b[Gal-Gal-T-Ag]-FCHASE, respectively). These unwanted poly-galactosylation products were seen in much great proportion on the simpler monosaccharide acceptors, and to a lesser extent with the GM2-FCHASE acceptor. The reaction conditions were optimized to minimize the poly-galactosylation of the peptide acceptor by keeping the concentration of donor in the reaction lower than 2 mM. The level of polygalactosylation was variable: whereas never more than 10% of the side products was observed on the peptide acceptor, more than 30% of the polygalactosylated product could be easily obtained with the monosaccharide acceptor.

The reaction products were analyzed by capillary electrophoresis mass spectrometry (CE-MS; FIG. 3A-B). The CE-MS spectrum of IFNα2b[Tn]-FCHASE (FIG. 3A) contains a singly-protonated molecular ion at m/z 1377.2 and a doubly-protonated ion at m/z 689.4. Doubly-protonated ions with sodium and potassium adducts were detected at m/z 700.3 and 708.3, respectively. In addition, ions corresponding to full-length IFNα2b-FCHASE and IFNα2b-FCHASE having lost its carboxy-terminal prolyl residue were also observed at m/z 1174.1 and 1059.0, respectively. The predominant species on the CE-MS spectrum of IFNα2b[T-Ag]-FCHASE were a singly-charged ion at m/z 1538.9, a doubly-protonated ion at m/z 770.0 with the corresponding ammonium adduct at m/z 778.7 (FIG. 3B). As expected, the molecular weight of IFNα2b[T-Ag]-FCHASE was 162 Dalton higher than that of IFNα2b[Tn]-FCHASE, thus confirming the galactosylation of the peptide by CgtB$_{OH4384}$ (Δ30, C-terminal MalE).

Example 10

Activity on the Protein IFNα2b[Tn]

Figure 4:
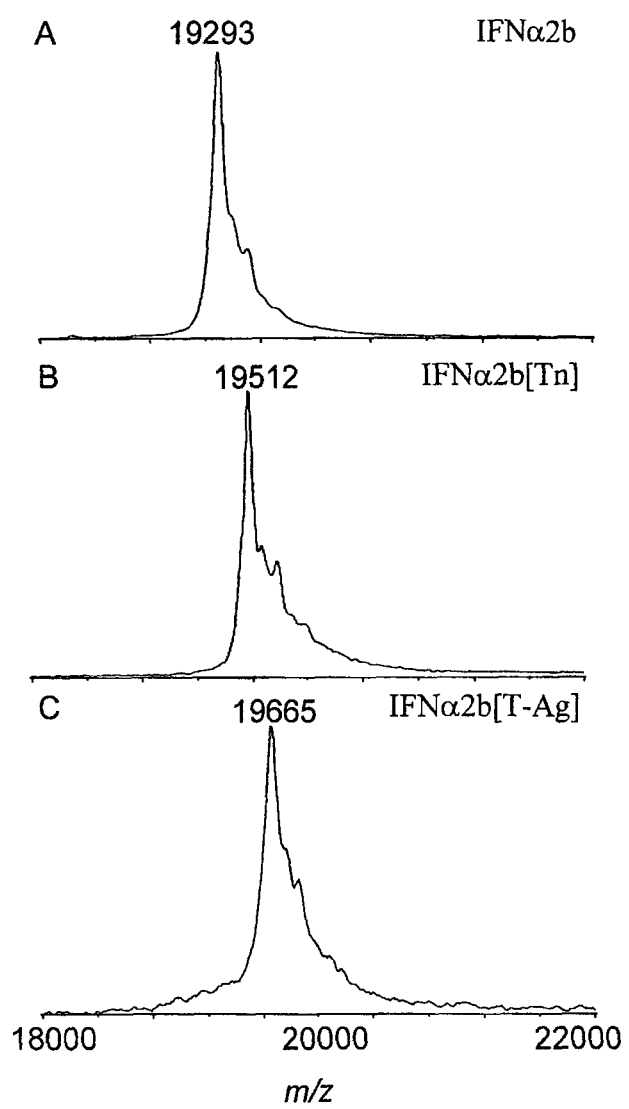
FIG. 4A illustrates the MALDI analysis of IFNα2b.
FIG. 4B illustrates the MALDI analysis of IFNα2b[Tn]
FIG. 4C illustrates the MALDI analysis of IFNα2b[T-Ag]

It is possible to glycosylate the IFNα2b protein in vitro (DeFrees, S. et al. *Glycobiology.* 16:833-843 (2006)). The improved CgtB (CJL-136) was therefore evaluated for making the Core 1 disaccharide on this protein. The MALDI spectra of IFNα2b (FIG. 4A) and IFNα2b[Tn] (FIG. 4B) present peaks at m/z 19293 and 19512, which are consistent with the expected molecular weights of IFNα2b and the corresponding glycosylated product. The MALDI spectrum of IFNα2b[T-Ag] (FIG. 4C), generated from the galactosylation of IFNα2b[Tn] by CgtB$_{OH4384}$ (Δ30, C-terminal MalE) shows a main species with a m/z of 19665, which is consistent with the presence of an additional hexosyl residue when compared to the main peak in FIG. 4B. The presence of the species at m/z 19665 is the proof that the IFNα2b[Tn] protein can be galactosylated by CJL-136. Within the limits of detection when using the non-labeled substrate, poly-galactosylated products were not produced.

Example 11

Poly-Galactosylation of the CgtB
β-1,3-Galactosyltransferase Products

Under some reaction conditions, CgtB$_{OH4384}$ adds a second Gal residue to oligosaccharide substrates, e.g., to a GM1a-derivatives synthesized from GM2-derivatives. The extent of addition of the second Gal is difficult to control but tends to be higher in long incubation times and in the presence of a large excess of donor. Since CgtB$_{OH4384}$ is much more active than CgtB11168 and CgtB$_{HS:10}$, it was unclear whether the second Gal addition was more obvious for CgtB$_{OH4384}$ or really absent in the case of CgtB$_{11168}$ and CgtB$_{HS:10}$. Using truncated CgtB constructs with MalE at the C-terminus, reactions were set up to obtain approximately 90% of GM1a (GA2 for CgtB$_{HS:10}$) after 60 minutes of incubation (see Table 5). Reaction mixtures included a 3-fold excess of donor (3 mM) over acceptor (1 mM). There were only traces of di-Gal product in the case of CgtB$_{11168}$ (Δ30, C-terminal MalE) and CgtB$_{HS:10}$ (Δ20, C-terminal MalE) after 60 minutes and after over-night incubations. The di-Gal product is obvious with CgtB$_{OH4384}$ (Δ30, C-terminal MalE) as soon as the GM2 and GM1a conversion yield was above 80%. The di-Gal product reached a plateau of approximately 25% in extended incubations.

TABLE V

Time-course reactions to measure poly-galactosylation by CgtB-MalE proteins.

| | CJL-136 with GM2-FCHASE CgtB$_{OH4384}$-30aa-MalE | | | CJL-137 with GM2-FCHASE CgtB$_{11168}$-30aa-MalE | | | CJL-177 with GA2-FCHASE CgtB$_{HS:10}$-20aa-MalE | | |
|---|---|---|---|---|---|---|---|---|---|
| Time (min) | GM2 (%) | GM1 (%) | Gal-GM1 (%) | GM2 (%) | GM1 (%) | Gal-GM1 (%) | GA2 (%) | GA1 (%) | Gal-GA1 (%) |
| 10 | 51.8 | 47.8 | 0.4 | 53.8 | 46.2 | 0.0 | 60.0 | 39.6 | 0.4 |
| 20 | 27.3 | 71.4 | 1.3 | 32.9 | 66.3 | 0.1 | 23.6 | 76.1 | 0.3 |
| 30 | 15.0 | 82.5 | 2.5 | 21.8 | 77.9 | 0.2 | 6.8 | 93.0 | 0.2 |
| 60 | 3.2 | 90.5 | 6.3 | 9.0 | 90.5 | 0.5 | 0.1 | 99.8 | 0.1 |
| o/n | 0.6 | 74.2 | 25.2 | 1.8 | 96.5 | 1.7 | 0.1 | 99.7 | 0.2 |

Example 12

In vitro Galactosylation of Human Growth Hormone

Figure 6:
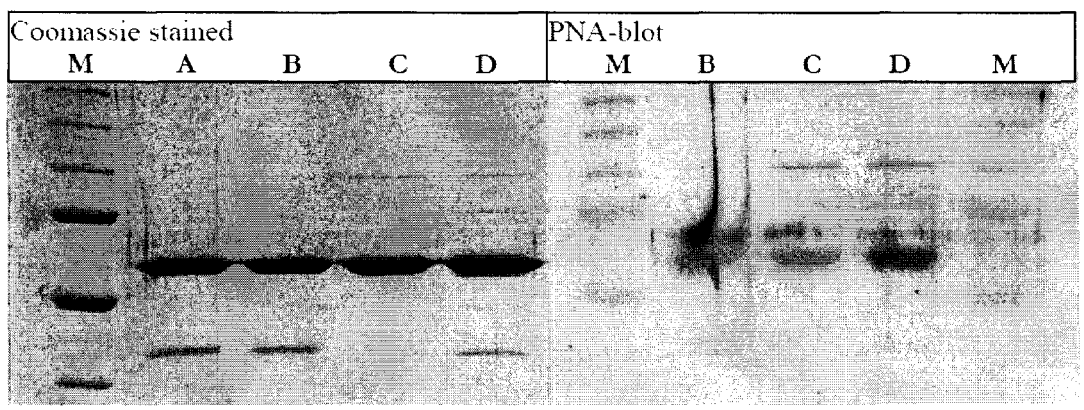
FIG. 6 depicts galactosylation of a human growth hormone (MalE-hGH) protein by the $CgtB_{11168}$ (Δ30, C-terminal MalE) protein. Samples were analyzed using SDS-PAGE separation followed by comassie staining (left side) and western blotting with a peanut agglutinin (right side). Lane A is one μg of a preparation of MalE-hGH that was kept at 4° C. for 4 months. Lane B is unglycosylated MalE-hGH. Lane C is [Tn]-MalE-hGH. Lane D is the galactosylated MalE-hGH product of the $CgtB_{11168}$ (Δ30, C-terminal MalE) reaction.

A MalE-human growth hormone (MalE-hGH) protein was expressed in *E. coli*. Human GalNAcT2 was also expressed in *E. coli* and used to glycosylate the MalE-hGH protein in vitro. The glycosylated MalE-hGH protein was concentrated and added to a reaction mixture that included 50 mM NaOAc (pH 6.0)+50 mM NaCl, 10 mM MnCl2 (from a freshly made stock), 1 mM DTT, 2.0 mM UDP-Gal and 6 milli-units of $CgtB_{11168}$ (Δ30, C-terminal MalE) were added and the reaction was incubated at room temperature (21° C.) for 23 hours. From the A280 data, the amount of fusion protein present was estimated to be 26 nmoles. Samples were analyzed using SDS-PAGE separation followed by comassie staining and western blotting with a peanut agglutinin that recognizes the T-Ag. About 1.0 µg of each preparation were loaded on gel for Coomassie staining and ~0.5 µg were used for the PNA-blot. One µg of a preparation of MalE-hGH that was kept at 4° C. for 4 months (A) was also loaded on the gel to determine the stability of the fusion protein under those storage conditions. Results are shown in FIG. 6, lanes A-D. Lanes B and C are unglycosylated MalE-hGH and [Tn]-MalE-hGH, respectively. ([Tn]-MalE-hGH is formed by action of the human GalNAcT2.) Lane D is the product of the $CgtB_{11168}$ (Δ30, C-terminal MalE) reaction. Increased staining in Lane D after PNA blotting indicates that the $CgtB_{11168}$ (Δ30, C-terminal MalE) protein galactosylated the MalE-hGH protein in vitro.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

SEQUENCE TABLE

SEQ ID NO: 1: Nucleotide sequence of β1,3-galactosyl-transferase-encoding ORF 6a of LOS biosynthesis locus from *C. jejuni* strain OH4384

```
ATGTTTAAAA TTTCAATCAT CTTACCAACT TATAATGTGG AACAATATAT   50
AGCAAGGGCA ATAGAAAGCT GTATCAATCA GACTTTTAAA GATATAGAAA  100
TAATTGTAGT TGATGATTGT GGAAATGATA ATAGTATAAA TATAGCCAAA  150
GAATACTCTA AAAAAGACAA AAGAATAAAA ATAATCCACA ATGAAAAAAA  200
CTTAGGTCTT TTAAGAGCAA GATATGAAGG TGTGAAAGTA GCAAACTCTC  250
CTTATATAAT GTTTTTAGAT CCTGATGATT ATTTGGAACT AAATGCTTGT  300
GAAGAGTGTA TAAAAATTTT AGATGAACAG GATGAAGTTG ATTTAGTGTT  350
TTTCAATGCT ATTGTTGAAA GTAATGTTAT TTCATATAAA AAGTTTGACT  400
TTAATTCTGG TTTTTATAGC AAAAAAGAGT TTGTAAAAAA AATTATTGCA  450
AAGAAAAATT TATATTGGAC TATGTGGGGG AAACTTATAA GAAAGAAATT  500
GTATTTAGAA GCTTTTGCGA GTTTAAGACT CGAGAAAGAT GTTAAAATCA  550
ATATGGCTGA AGATGTATTG TTATATTATC CAATGTTAAG TCAAGCTCAA  600
AAAATAGCAT ATATGAACTG TAATTTATAT CATTACGTGC CTAATAATAA  650
TTCAATTTGT AATACTAAGA ATGAAGTGCT TGTTAAAAAT AATATTCAAG  700
AGTTGCAGTT GGTTTTAAAC TATTTAAGGC AACAATATAT TTTAAACAAG  750
TATTGTAGCG TTCTCTATGT GCTAATTAAA TATTTGCTAT ATATTCAAAT  800
ATATAAAATA AAAAGAACAA AATTAATGGT TACATTATTA GCTAAAATAA  850
ATATTTTAAC TTTAAAAATT TTATTTAAAT ATAAAAAATT TTTAAAACAA  900
TGTTAA                                                  906
```

SEQ ID NO: 2 Amino acid sequence of β1,3-galactosyltransferase encoded by ORF 6a of LOS biosynthesis locus from *C. jejuni* strain OH4384

```
                10         20         30         40         50
  1 MFKISIILPT YNVEQYIARA IESCINQTFK DIEIIVVDDC GNDNSINIAK
 51 EYSKKDKRIK IIHNEKNLGL LRARYEGVKV ANSPYIMFLD PDDYLELNAC
101 EECIKILDEQ DEVDLVFFNA IVESNVISYK KPDFNSGFYS KKEFVKKIIA
151 KKNLYWTMWG KLIRKKLYLE AFASLRLEKD VKINMAEDVL LYYPMLSQAQ
201 KIAYMNCNLY HYVPNNNSIC NTKNEVLVKN NIQELQLVLN YLRQNYILNK
251 YCSVLYVLIK YLLYIQIYKI KRTKLMVTLL AKINILTLKI LFKYKKFLKQ
301 C
```

SEQ ID NO: 3 Nucleotide sequence of β1,3-galactosyltransferase from *C. jejuni* strain O: 4 ATCC 43432

```
atgtttaaaatttcaatcatcttaccaacttataatgtggaacaatatatagcaagggcaat
agaaagctgtatcaatcagacttttaaagatatagaaataattgtagttgatgattgtggaa
atgataatagtataaatatagccaaagaatactctaaaaaagacaaaagaataaaaataatc
cacaatgaaaaaaacttaggtcttttaagagcaagatatgaaggtgtgaaagtagcaaactc
tccttatataatgtttttagatcctgatgattatttggaactaaatgcttgtgaagagtgta
taaaaattttagatgaacaggatgaagttgatttagtgttttttcaatgctattgttgaaagt
aatgttatttcatataaaaagtttgactttaattctggttttttatagcaaaaaagagtttgt
gaaaaaaattattgcaaagaaaaatttatattggactatgtgggggaaacttataagaaaga
aattgtatttagaagcttttgcgagtttaaaactcgagaaagatgttaaaatcaatatggct
```

SEQUENCE TABLE

```
gaagatgtattgttatattatccaatgttaagtcaagctcaaaaaatagcatatatgaactg
taatttatatcattacgtgcctaataataattcaatttgtaatactaagaatgaagtgcttg
ttaaaaataatattcaagagttgcagttggttttaaactatttaaggcaaaattatatttta
aacaagtattgtagcgttctctatgtgctaattaaatatttgctatatattcaaatatataa
aataaaaagaacaaaattaatggttacattgttagctaaaataaatattttaactttaaaaa
ttttatttaaatataaaaaattttaaaacaatgttaa
```

SEQ ID NO: 4 Protein sequence of β,3-galactosyltransferase from *C. jejuni* strain O: 4 ATCC 43432
```
MFKISIILPTYNVEQYIARAIESCINQTFKDIEIIVVDDCGNDNSINIAKEYSKKDKRIKII
HNEKNLGLLRARYEGVKVANSPYIMFLDPDDYLELNACEECIKILDEQDEVDLVFFNAIVES
NVISYKKFDFNSGFYSKKEFVKKIIAKKNLYWTMWGKLIRKKLYLEAFASLKLEKDVKINMA
EDVLLYYPMLSQAQKIAYMNCNLYHYVPNNNSICNTKNEVLVKNNIQELQLVLNYLRQNYIL
NKYCSVLYVLIKYLLYIQIYKIKRTKLMVTLLAKINILTLKILFKYKKFLKQC
```

SEQ ID NO: 5 Nucleotide sequence of (β,3-galactosyltransferase from C. jejuni strain O: 41 ATCC 43460
```
atgtttaaaatttcaatcatcttaccaacttataatgtggaacaatatatagcaagggcaat
agaaagctgtatcaatcagacttttaaagatatagaaataattgtagttgatgattgtggaa
atgataatagtataaatatagccaaagaatactctaaaaaagacaaaagaataaaaataatc
cacaatgaaaaaaacttaggtctcttttaagagcaagatatgaaggtgtgaaagtagcaaactc
tccttatataatgttttttagatcctgatgattatttggaactaaatgcttgtgaagagtgta
taaaaattttagatgaacaggatgaagttgattttagtgtttttcaatgctattgttgaaagt
aatgttatttcatataaaaagtttgactttaattctggtttttatagcaaaaaagagtttgt
aaaaaaaaattattgcaaataaaaatttatattggactatgtggggggaaacttataagaaaga
aattgtatttagaagcttttgcgagtttaagactcgagaaagatgttaaaatcaatatggct
gaagatgtattgttatattatccaatgttaagtcaagctcaaaaaatagcatatatgaactg
taatttatatcattacgtgcctaataataattcaatttgtaatactaagaatgaagtgcttg
ttaaaaataatattcaagagttgcagttggttttaaactatttaaggcaaaattatatttta
aacaagtattgtagcgttctctatgtgctaattaaatatttgctatatattcaaatatataa
aataaaaagaacaaaattaatggttacattattagctaaaataaatattttaactttaaaaa
ttttatttaaatataaaaaattttaaaacaatgttaa
```

SEQ ID NO: 6 Protein sequence of β1,3-galactosyltransferase from *C. jejuni* strain O: 41 ATCC 43460
```
MFKISIILPTYNVEQYIARAIESCINQTFKDIEIIVVDDCGNDNSINIAKEYSKKDKRIKII
HNEKNLGLLRARYEGVKVANSPYIMFLDPDDYLELNACEECIKILDEQDEVDLVFFNAIVES
NVISYKKFDFNSGFYSKKEFVKKIIANKNLYWTMWGKLIRKKLYLEAFASLRLEKDVKINMA
EDVLLYYPMLSQAQKIAYMNCNLYHYVPNNNSICNTKNEVLVKNNIQELQLVLNYLRQNYIL
NKYCSVLYVLIKYLLYIQIYKIKRTKLMVTLLAKINILTLKILFKYKKFLKQC
```

SEQ ID NO: 7 Nucleotide sequence of β1,3-galactosyltransferase from *C. jejuni* strain NCTC 11168 DNA
```
atgagtcaaatttccatcatactaccaacttataatgtggaaaaatatattgctagagcatt
agaaagttgcattaaccaaacttttaaagatatagaaatcattgtagtagatgattgtggta
atgataaaagtatagatatagctaaagagtatgctagtaaagatgatagaataaaaatcata
cataatgaagagaatttaaagcttttaagagcaagatatgaaggtgctaaagtagcaacttc
accttatatcatgtttttagattctgatgattatttagaacttaatgcttgcgaagaatgta
ttaaaattttggatatgggtgggggggtaaaattgatttgttgtgtttttgaagcttttatt
accaatgcaaaaaaatcaataaaaaaattaaatataaaacaaggaaaatacaacaacaaaga
atttacaatgcaaatacttaaaactaaaaatccattttggacaatgtgggctaaaataatca
aaaaagatatttatttaaaagccttcaacatgttaaatctcaaaaaagaaatcaaaataaat
atggcagaagatgccttattatattatcctttgacaatattatctaatgaaatattttactt
aacacaacctttgtatacccagcatgtaaatagcaattctataacaaataatattaattctt
tagaagctaatattcaagaacataaaattgttttaaatgttttaaaatcaattaaaaataaa
aaaacacctctatattttctaattatatatttattaaaaaattcaattattgaaatatgaaca
aaattttaataaaagaaatataaatcttatttattataaaataaatattttatatcaaaaat
atcaattcaaatggaaaaaattttttatataatttaattccgtaa
```

SEQ ID NO: 8 Protein sequence of β1,3-galactosyltransferase from *C. jejuni* strain NCTC 11168
```
MSQISIILPTYNVEKYIARALESCINQTFKDIEIIVVDDCGNDKSIDIAKEYASKDDRIKII
HNEENLKLLRARYEGAKVATSPYIMFLDSDDYLELNACEECIKILDMGGGGKIDLLCFEAFI
TNAKKSIKKLNIKQGKYNNKEFTMQILKTKNPFWTMWAKIIKKDIYLKAFNMLNLKKEIKIN
MAEDALLYYPLTILSNEIFYLTQPLYTQHVSNSITNNINSLEANIQEHKIVLNVLKSIKNK
KTPLYFLIIYLLKIQLLKYEQNFNKRNINLIYYKINILYQKYQFKWKKFLYNLIP
```

SEQ ID NO: 9 Nucleotide sequence of β1,3-galactosyltransferase from *C. jejuni* strain HS:10 ATCC 43438 DNA
```
atgtttaaaatttcaatcatcttgccaacttataatgtggaacaatatatagcaagggcaat
agaaagttgtatcaatcagacttttaaaaatatagaaataattgtagttgatgattgtggaa
gtgacaaaagtatagatatagttaaagaatatgccaaaaaagatgatagaataaaaatcata
cataatgaagaaaatttaaaacttttaagagctagatatgaaggtgtaaaagtagcaaactc
tccttatataatgttttttagatcctgatgattatttagaacttaatgcttgtgaagaatgta
tgaaaatttttaaaaaacaatgaatagattattatttttaatgcatttgtattggaaaat
aacaataaaaatagaagaaagttgaattttcaagaaaaatgttatgtaaaaaaagatttttt
aaaagaactattaaaaactaaaaattatttggacagtgtgggcaaagtcataaaaaaag
aattatatctcaaggctgttggtttaatatcgctagaaaatgctaaaataaatatggctgaa
```

SEQUENCE TABLE

```
gatgttttattatattaccctttgataaatatttcaaatactatatttcacttgagtaaaaa
tttatacaattatcaaataaataatttctctataaccaaaacattaacattgcaaaatataa
aaacaaatatacaagaacaagataatgttctatatcttctaaagaagatgcaatataattac
aattttaacttaactttgcttaaattaattgagtattttttattaattgaaaaatactcatt
atcaagcaagcgaaatgttctttgttttaaaatcaatattttttttaaaaaaatccaattta
aattttatcgcttgctgaagatgtaa
```

SEQ ID NO: 10 Protein sequence of β1,3-galactosyltransferase from *C. jejuni* strain HS:10 ATCC 43438
```
MFKISIILPTYNVEQYIARAIESCINQTFKNIEIIVVDDCGSDKSIDIVKEYAKKDDRIKII
HNEENLKLLRARYEGVKVANSPYIMFLDPDDYLELNACEECMKILKNNEIDLLFFNAFVLEN
NNKIERKLNFQEKCYVKKDFLKELLKTKNLFWTVWAKVIKKELYLKAVGLISLENAKINMAE
DVLLYYPLINISNTIFHLSKNLYNYQINNFSITKTLTLQNIKTNIQEQDNVLYLLKKMQYNY
NFNLTLLKLIEYFLLIEKYSLSSKRNVLCFKINIFFKKIQFKFYRLLKM
```

SEQ ID NO: 11: 5'-end primer for amplifying cgtB from *C. jejuni* OH4384
CTTAGGAGGTCATATGTTTAAAATTTCAATCATCTTACC SEQ ID NO: 12: 3'-end primer for amplifying cgtB from *C. jejuni* OH4384
CCTAGGTCGACCTCTAAAAAAAATATTCTTAACATTG SEQ ID NO: 13: 5'-end primer for amplifying cgtB from *C. jejuni* NCTC 11168
CTTAGGAGGTCATATGAGTCAAATTTCCATCATACTACC SEQ ID NO: 14: 3'-end primer for amplifying cgtB from *C. jejuni* NCTC1168
CCTAGGTCGACTTACGGAATTAAATTATATAAAAATTTTTTCC 3'

SEQ ID NO: 15: 5'-end primer for amplifying cgtB from *C. jejuni* HS:10
GCTGCTGGACATATGTTTAAAATTTCAATCATCTTGCC SEQ ID NO: 16: 3'-end primer for amplifying cgtB from *C. jejuni* HS:10
CTTAGCGTCGACTTATTACATCTTCAGCAAGCGATAAAATTTAAATTG SEQ ID NO: 17: SCJ-319: 5'-end primer for amplifying cgtB from *C. jejuni* NCTC 11168 GCTGCTGGACATATGAGTCAAATTTCCATCATACTACCAAC SEQ ID NO: 18: SCJ-322: 3'-end primer for amplifying cgtB from *C. jejuni* OH4384
CTTAGCGTCGACTTAACATTGTTTTAAAAATTTTTTATATTT SEQ ID NO: 19: SCJ-368: 3'-end primer for amplifying cgtB from *C. jejuni* NCTC 11168 CTTAGCGTCGACTTATTTGAATTGAGATTTTTGATATAAAATATT SEQ ID NO: 20: SCJ-369: 3'-end primer for amplifying cgtB from *C. jejuni* NCTC 11168 CTTAGCGTCGACTTATATTTTATAATAAATAAGATTTATATTTCT SEQ ID NO: 21: SCJ-370: 3'-end primer for amplifying cgtB from *C. jejuni* NCTC 11168 CTTAGCGTCGACTTATTTATTAAAATTTTGTTCATATTTCAATAA SEQ ID NO: 22: SCJ-400: 5'-end primer for amplifying cgtB from *C. jejuni* OH4384
GCTGCTGGACATATGTTTAAAATTTCAATCATCTTACCAAC SEQ ID NO: 23: SCJ-401: 3'-end primer for amplifying cgtB from *C. jejuni* OH4384
CTTAGCGCTGACTTATAAAATTTTTAAAGTTAAAATATTTATT SEQ ID NO: 24: SCJ-402: 3'-end primer for amplifying cgtB from *C. jejuni* OH4384
CTTAGCGTCGACTTAAGCTAATAATGTAACCATTAATTTTGTT SEQ ID NO: 25: SCJ-403: 3'-end primer for amplifying cgtB from *C. jejuni* OH4384
CTTAGCGTCGACTTATTTTATTTTATATATTTGAATATATAGC SEQ ID NO: 26: SCJ-404: 3'-end primer for amplifying cgtB from *C. jejuni* HS:10
CTTAGCGTCGACTTAGATTTTTTAAAAAAAATATTGATTTTA SEQ ID NO: 27: SCJ-405: 3'-end primer for amplifying cgtB from *C. jejuni* HS:10
CTTAGCGTCGACTTAACAAAGAACATTTCGCTTGCTTGATAAT SEQ ID NO: 28: SCJ-406: 3'-end primer for amplifying cgtB from *C. jejuni* HS:10
CTTAGCGTCGACTTAGTATTTTCAATTAATAAAAAATACTCA SEQ ID NO: 29: SCJ-408: primer for amplifying cgtB from *C. jejuni* OH4384
CCGGAATTCCGGTTTTATTTTATATATTTGAATATATAGC SEQ ID NO: 30: SCJ-410: primer for amplifying cgtB from *C. jejuni* NCTC 11168
CCGGAATTCCGGTTTATTAAAATTTTGTTCATATTTCAATAA SEQ ID NO: 31: SCJ-452: primer for amplifying cgtB from *C. jejuni* HS:10
CCGGAATTCGCCACAAAGAACATTTCGCTTGCTTGATAATGAG

SEQUENCE TABLE

SEQ ID NO: 32: malE5p: primer for amplifying malE
GAAACAGGATCCATCGATGCTTAGGAGGTCAGATGAAAATCGAAGAAGGTA
AACTGG SEQ ID NO: 33: malE3p: 5'-end primer for amplifying malE
ACGAATCCTCCACATATGTCCGCCACCCTTGGTGATACGAGTCTGCGC SEQ ID NO: 34: malE3pSalI: 3'-end primer for amplifying malE
GGGGGGGGGGTCGACTTATTACTTGGTGATACGAGTCTGCGCGTCTTC SEQ ID NO: 35: malE5pEcoRI: primer for amplifying malE
GGGGGGGGGGAATTCAAAATCGAAGAAGGTAAACTGGTAATCTGC

What is claimed is:

1. A β-1,3-galactosyltransferase fusion polypeptide comprising
   i. a truncated CgtB polypeptide, wherein between 1 and 35 amino acids are removed from the C terminal end of the CgtB polypeptide, and
   ii. a maltose binding protein domain fused to the C-terminus of the CgtB polypeptide, wherein the β-1,3-galactosyltransferase polypeptide transfers a galactose moiety from a donor substrate to an acceptor substrate and wherein the truncated CgtB polypotide comprises an amino acid sequence with at least 90% identity to an amino acid sequence selected from the group consisting of SEQ ID NO:2, SEQ ID NO:4, SEQ ID NO:6, SEQ ID NO:8 and SEQ ID NO: 10.

2. The β-1,3-galactosyitransferase fusion polypeptide of claim 1, wherein the truncated CgtB polypeptide comprises an amino acid sequence with at least 95% identity to an amino acid sequence selected from the group consisting of SEQ ID NO:2, SEQ ID NO:4, SEQ ID NO:6, SEQ ID NO:8 and SEQ ID NO: 10.

3. The β-1,3-gatactosyltransferase fusion polypeptide of claim 1, wherein the acceptor substrate is a glycopeptide, a glycoprotein, a glycolipids, or a ganglioside.

4. The β-1,3-galactosyltransferase fusion polypeptide of claim 1, wherein the truncated CgtB polypeptide comprises an amino acid sequence with at least 90% identity to amino acids 1-266 of SEQ ID NO:2.

5. The β-1,3-galactosyltransferase fusion polypeptide of claim 1, wherein the truncated CgtB polypeptide comprises an amino acid sequence with at least 90% identity to amino acids 1-271 of SEQ ID NO:2.

6. The β-1,3-galactosyltransferase polypeptide of claim 4, wherein the truncated CgtB polypeptide comprises an amino acid sequence with at least 95% identity to amino acids 1-266 of SEQ ID NO:2.

7. The β-1,3-gatactosyltransferase polypeptide of claim 5, wherein the truncated CgtB polypeptide comprises an amino acid sequence with at least 91% identity to amino acid residues 1-271 of SEQ ID NO:2.

8. The β-1,3-gaiactosyltransferase polypeptide of claim 5, wherein the truncated CgtB polypeptide comprises the amino acid sequence of amino acid residues 1-271 of SEQ ID NO:2.

9. A method of producing a galactosylated product saccharide, the method comprising the step of:
   a. contacting an acceptor substrate with a donor substrate comprising a galactose moiety and the β-1,3-galactosyltransferase polypeptide of claim 1; and
   b. allowing transfer of the galactose moiety to the acceptor saccharide to occur, thereby producing the galactosylated product saccharide.

10. A method of producing a galactosylated protein or peptide, the method comprising the step of:
   a. contacting an acceptor substrate with a donor substrate comprising a galactose moiety and the β-1,3-galactosyltransferase polypeptide of claim 1; and
   b. allowing transfer of the galactose moiety to the acceptor saccharide to occur, thereby producing the galactosylated protein or peptide.

11. A method of producing a galactosylated glycolipid or ganglioside, the method comprising the step of:
   a. contacting an acceptor substrate with a donor substrate comprising a galactose moiety and the P-1,3-galactosyltranslerase polypeptide of claim 1; and
   b. allowing transfer of the galactose moiety to the acceptor saccharide to occur, thereby producing the galactosylated glycolipid or ganglioside.

12. The β-1,3-galactosyltransferase fusion polypeptide of claim 1, wherein the CgtB polypeptide comprises an amino acid sequence selected from the group consisting of SEQ ID NO:2, SEQ ID NO:4, SEQ ID NO:6, SEQ ID NO:8 and SEQ ID NO: 10.

* * * * *